(12) United States Patent
Kitano et al.

(10) Patent No.: US 9,684,764 B2
(45) Date of Patent: Jun. 20, 2017

(54) DATA COMMUNICATION SYSTEM, DATA ANALYSIS APPARATUS, DATA COMMUNICATION METHOD, AND PROGRAM PRODUCT

(71) Applicants: Okinawa Institute of Science and Technology Graduate University, Okinawa (JP); SBX Corporation, Tokyo (JP); The Systems Biology Institute, Tokyo (JP)

(72) Inventors: Hiroaki Kitano, Okinawa (JP); Samik Ghosh, Tokyo (JP); Yukiko Matsuoka, Tokyo (JP)

(73) Assignees: Okinawa Institute of Science and Technology Graduate University, Okinawa (JP); SBX Corporation, Tokyo (JP); The Systems Biology Institute, Tokyo (JP)

( * ) Notice: Subject to any disclaimer, the term of this patent is extended or adjusted under 35 U.S.C. 154(b) by 0 days.

(21) Appl. No.: 14/433,721

(22) PCT Filed: Nov. 7, 2013

(86) PCT No.: PCT/JP2013/080146
§ 371 (c)(1),
(2) Date: Apr. 6, 2015

(87) PCT Pub. No.: WO2014/073617
PCT Pub. Date: May 15, 2014

(65) Prior Publication Data
US 2015/0278451 A1  Oct. 1, 2015

(30) Foreign Application Priority Data
Nov. 7, 2012  (JP) .................................. 2012-245326

(51) Int. Cl.
*G06F 7/04* (2006.01)
*G06F 19/00* (2011.01)
(Continued)

(52) U.S. Cl.
CPC ...... *G06F 19/322* (2013.01); *G06F 17/30876* (2013.01); *G06F 21/6218* (2013.01); *G06F 21/6245* (2013.01); *G06F 2221/2113* (2013.01)

(58) Field of Classification Search
None
See application file for complete search history.

(56) References Cited

U.S. PATENT DOCUMENTS

| | | | |
|---|---|---|---|
| 2003/0036683 A1* | 2/2003 | Kehr ..................... | G06F 19/325 600/300 |
| 2006/0084847 A1* | 4/2006 | Reed ..................... | A61B 5/0002 600/300 |

FOREIGN PATENT DOCUMENTS

| | | |
|---|---|---|
| GB | 2 444 410 A | 6/2008 |
| JP | 2006 185311 | 7/2006 |

OTHER PUBLICATIONS

Ikarashi, et al., "A Hybrid Anonymization with Secure Computation and Randomization", The 29th Symposium on Cryptography and Information Security, (Jan. 30-Feb. 2, 2012), pp. 1-8.
(Continued)

*Primary Examiner* — Brandon Hoffman
(74) *Attorney, Agent, or Firm* — Oblon, McClelland, Maier & Neustadt, L.L.P.

(57) ABSTRACT

In a plurality of data analysis apparatuses communicatively coupled to one another, a database is accessed at a given access level. Based on the data acquired from the database, an application program is executed to perform data analysis. Communication control is performed to allow transmission
(Continued)

and reception of a data analysis result with respect to another data analysis apparatus at a different access level.

9 Claims, 18 Drawing Sheets

(51) Int. Cl.
*G06F 21/62* (2013.01)
*G06F 17/30* (2006.01)

(56) References Cited

OTHER PUBLICATIONS

Sakuma, et al., "Privacy-Preserving Data Mining", Journal of Japanese Society for Artificial Intelligence, vol. 24, No. 2, (2009), pp. 283-294.

Urabe, et al., "A Collusion-Resistant Approach to Distributed Privacy-Preserving Data Mining", IPSJ SIG Technical Reports, vol. 2006, No. 42, (May 11, 2006), pp. 33-37 (with English abstract).

Nanji, et al., "Security Challenges of Electronic Medical Records", Computerworld, URL: http://www.computerworld.com/s/article/9128261/Security_Challenges_of_Electronic_Medical_Records?taxonomyId=17&pageNumber=1, (Feb. 19, 2009), Total 5 Pages.

Carey, et al., "Persistent Security, Privacy, and Governance for Healthcare Information", Health Sec'11, $2^{ND}$ USENIX Workshop on Health Security and Privacy, (Aug. 9, 2011), Total 4 Pages.

"Oracle Label Security with Oracle Database 11g Release 2", URL: http://www.oracle.com/technetwork/database/security/owp-security-label-security-11gr2-133601.pdf?ssSourceSiteId=ocomjp, (Sep. 2009), Total 12 Pages.

International Search Report and Written Opinion of the International Searching Authority Issued Feb. 10, 2014 in PCT/JP13/080146 Filed Nov. 7, 2013.

Extended European Search Report issued Apr. 19, 2016 in Patent Application No. 13853788.1.

Alejandro Flores "Secure exchange of information in electronic health records" University of Wollongong (PhD thesis), http://ro.uow.edu.au/cgi/viewcontent.cgi?article=4308&context=theses, XP055263354, Dec. 31, 2010, pp. 1-202 and Cover Pages.

\* cited by examiner

DATA COMMUNICATION SYSTEM, DATA ANALYSIS APPARATUS, DATA COMMUNICATION METHOD, AND PROGRAM PRODUCT

CROSS-REFERENCE TO RELATED APPLICATIONS

This application is a 371 of International App. No. PCT/JP2013/080146, filed Nov. 7, 2013. This application also claims priority to Japanese App. No. JP2012-245326, filed Nov. 7, 2012. The entire content and disclosure of each of the foregoing applications is incorporated herein by reference.

TECHNICAL FIELD

The present invention relates to a data communication system, a data analysis apparatus, a data communication method, and a program product.

BACKGROUND ART

Conventionally, a technique related to appropriate handling of data such as medical-related information that needs information management is developed.

Non Patent Literature 1 discloses that data is protected by access restriction depending on user qualification for a security problem with medical-related electronic recording.

Non Patent Literature 2 discloses the system that provides access to the resource derived from an original resource to ensure security and privacy.

Non Patent Literature 3 discloses that a label is given to data and a user label is assigned to allow access to a plurality of databases at given levels.

CITATION LIST

Non Patent Literature

Non Patent Literature 1: F Nanji "Security challenges of electronic medical records" ComputerWorld, 2009

Non Patent Literature 2: W. Knox Carey, Jarl Nilsson, and Steve Mitchell "Persistent Security, Privacy, and Governance for Healthcare Information" Health Sec'11, 2nd USENIX Workshop on Health Security and Privacy, Aug. 9, 2011

Non Patent Literature 3: Oracle and/or its affiliates, "Oracle Label Security with Oracle Database 11g Release 2", [online], 2009, Oracle, Oracle Web site, [searched on Oct. 24, 2012], Internet <URL:http://www.oracle.com/technetwork/database/security/owp-security-label-security-11gr2-133601.pdf?ssSourceSiteId=ocomjp>

SUMMARY OF INVENTION

Problem to be Solved by the Invention

However, the conventional security method allows the access corresponding to the security level simply given to the data such as medical information but has the problem where it is difficult to hand over analyzed data between persons or organizations having different access levels.

Solution to Problem

The present invention has been made in view of the above-described circumstances, and it is an object of the present invention to provide a data communication system, a data analysis apparatus, a data communication method, and a program that disclose disclosable data to allow analysis while protecting data as a secret target and that allow notifying persons, organizations, or the like having different access levels about information that is obtained as a result.

Means for Solving Problem

In order to attain this object, a data communication system according to one aspect of the present invention is a data communication system where a plurality of data analysis apparatuses is communicatively coupled to one another, the data analysis apparatus including a storage unit and a control unit, wherein the storage unit includes a database that stores data, and the control unit includes a data accessing unit that accesses the database at a given access level, a program executing unit that executes an application program based on the data acquired from the database via the data accessing unit to perform data analysis, and a communication controlling unit that performs communication control to allow transmission and reception of a data analysis result by the program executing unit with respect to another of the data analysis apparatuses where the access level is different.

The data communication system according to another aspect of the present invention is the data communication system, wherein the data accessing unit includes a micro-module group that accesses the database at respective different access levels.

The data communication system according to still another aspect of the present invention is the data communication system, wherein the other of the data analysis apparatus has the given access level that is high to allow specifying a target, and the program executing unit of the other of the data analysis apparatus refers to the database based on the received data analysis result to specify a target and output notification.

The data communication system according to still another aspect of the present invention is the data communication system, wherein while the program executing unit executes the application program in a master mode, the program executing unit of another of the data analysis apparatuses executes the application program in a slave mode based on acquisition of the data depending on the access level at the master mode side via the data accessing unit.

The data communication system according to still another aspect of the present invention is the data communication system, wherein the database is a personal health database that stores medical information including one of medical record information, drug prescription data, medication intake data, health examination data, subjective symptom information, and behavior record data of an individual person, as the data.

The data communication system according to still another aspect of the present invention is the data communication system, wherein the program executing unit performs the data analysis using one data analysis method of Genome Wide Association Study (GWAS), Conditional Genome-Wide Association Study (conditional GWAS), Genome-Wide Network-based Association Study (GNAS), and Conditional GNAS.

The data communication system according to still another aspect of the present invention is the data communication system, wherein the access level that allows specifying a target is given to a person related to a medical institution including a doctor, and the access level that does not allow specifying a target is given to a user of a database open to an outside.

A data analysis apparatus according to still another aspect of the present invention is a data analysis apparatus comprising a storage unit, and a control unit, the data analysis apparatus being communicatively coupled to other data analysis apparatuses, wherein the storage unit includes a database that stores data, and the control unit includes a data accessing unit that accesses the database at a given access level, a program executing unit that executes an application program based on the data acquired from the database via the data accessing unit to perform data analysis, and a communication controlling unit that performs communication control to allow transmission and reception of a data analysis result by the program executing unit with respect to another of the data analysis apparatuses where the access level is different.

A data communication method according to still another aspect of the present invention is a data communication method executed by a data communication system where a plurality of data analysis apparatuses is communicatively coupled to one another, the data analysis apparatus including a storage unit and a control unit, wherein the storage unit includes a database that stores data, and the method executed by the data communication system comprises a data accessing step of accessing the database at a given access level, the data accessing step being executed by the control unit of one of the data analysis apparatus in the plurality of data analysis apparatuses, a program executing step of executing an application program based on the data acquired from the database at the data accessing step to perform data analysis, the program executing step being executed by the control unit of the one of the data analysis apparatus, a communication controlling step of transmitting a data analysis result at the program executing step to another of the data analysis apparatuses where the access level is different, the communication controlling step being executed by the control unit in the one of the data analysis apparatus, and a communication controlling step of receiving the data analysis result from the one of the data analysis apparatus, the communication controlling step being executed by the control unit of the other of the data analysis apparatus.

A computer program product according to still another aspect of the present invention is a computer program product having a non-transitory tangible computer readable medium including programmed instructions for causing, when executed by a data analysis apparatus including a storage unit that includes a database storing data, and a control unit, the data analysis apparatus being communicatively coupled to other data analysis apparatuses, the control unit to perform a data communication method comprising a data accessing step of accessing the database at a given access level, a program executing step of executing an application program based on the data acquired from the database at the data accessing step to perform data analysis, and a communication controlling step of performing communication control to allow transmission and reception of a data analysis result at the program executing step with respect to another of the data analysis apparatuses where the access level is different.

Effect of the Invention

According to the present invention, in the system where a plurality of data analysis apparatuses are communicatively coupled to one another, an application program is executed to perform data analysis based on the data acquired from a database via a data accessing unit that access the database at a given access level. Communication control is performed to allow transmission and reception of a data analysis result with respect to another data analysis apparatus at a different access level. Accordingly, the present invention provides an effect that allows analysis by disclosing disclosable data while protecting data as a secret target and that allows notifying persons, organizations, or the like having different access levels about the information obtained as a result.

According to the present invention, in the above description, the data accessing unit includes a micromodule group that accesses the database at respective different access levels. This allows dealing with various access levels using a common module, thus accepting various applications and uses of the user. This provides an effect excellent in versatility.

According to the present invention, in the above description, the other of the data analysis apparatus has the give access level that is high to allow specifying a target. The program executing unit of the other of the data analysis apparatus refers to the database based on the received data analysis result to specify the target and output notification. This provides an effect that allows specifying the target when notification is needed, based on the analysis result performed by the application or the user having a low access level.

According to the present invention, in the above description, medical information including one of medical record information, drug prescription data, medication intake data, health examination data, subjective symptom information, and behavior record data of an individual person is stored as the data. This provides an effect that allows providing the database use where security is ensured while handling the personal information in a medical field as the analysis target.

According to the present invention, in the above description, the data analysis is performed using one data analysis method of Genome Wide Association Study (GWAS), Conditional Genome-Wide Association Study (conditional GWAS), Genome-Wide Network-based Association Study (GNAS), and Conditional GNAS. This provides an effect that allows performing genome analysis where security is ensured while handling personal genome information.

According to the present invention, in the above description, the access level that allows specifying a target is given to a person related to a medical institution including a doctor. The access level that does not allow specifying a target is given to a user of a database open to an outside. This provides an effect that allows accelerating open innovation by opening the database use at a restricted access level also to the user other than the person related to the medical institution.

BRIEF DESCRIPTION OF DRAWINGS

FIG. 14 is a diagram of an information sharing system example between the departments of a pharmaceutical company or the like;

MODE(S) FOR CARRYING OUT THE INVENTION

Figure 1:
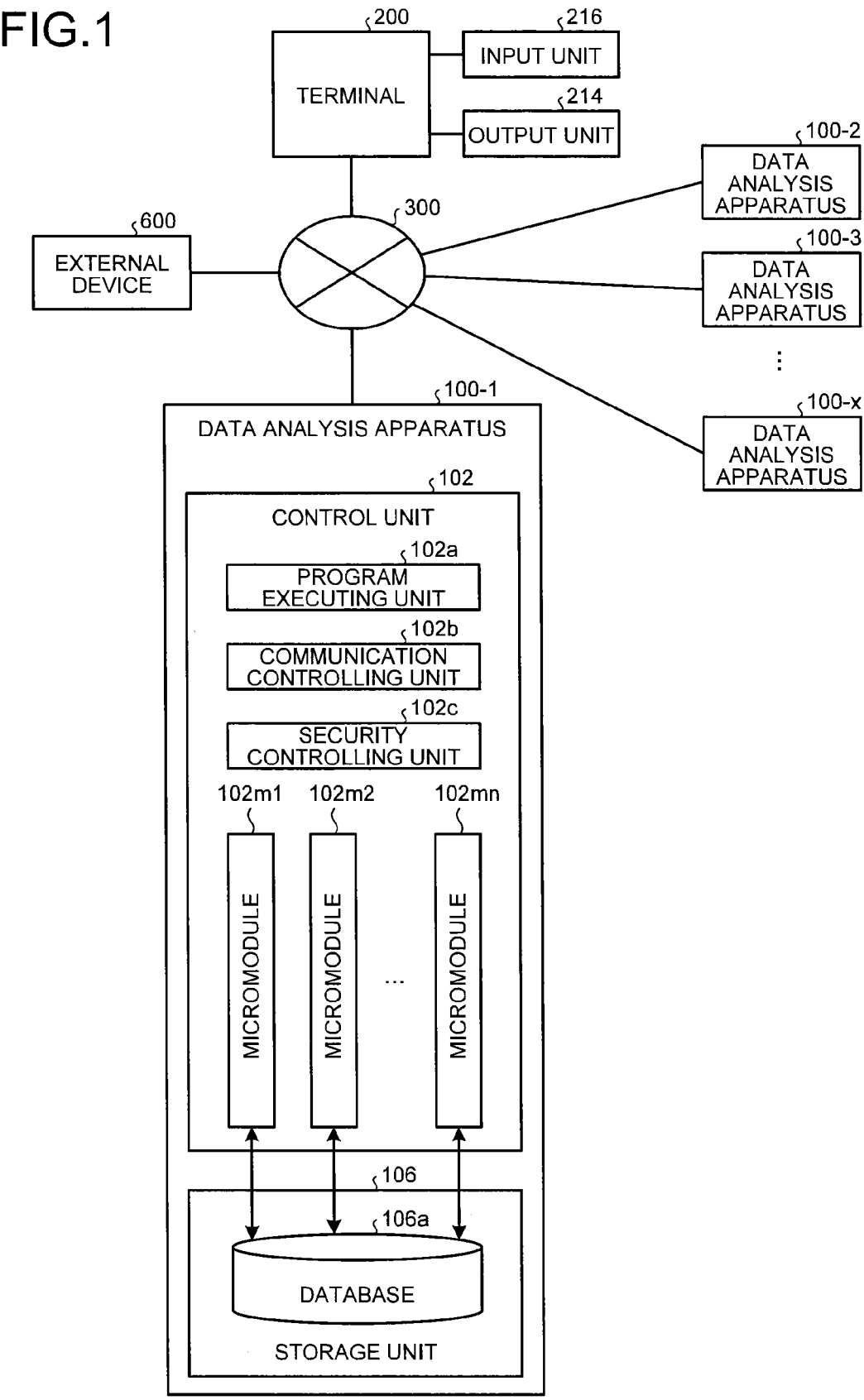
FIG. 1 is a block diagram of an example of the configuration of a data communication system according to this embodiment.

Hereinafter, the details of an embodiment of a data communication system, a data analysis apparatus, a data communication method, and a program product according to the present invention will be explained. The present invention is not limited to these embodiments.

Outline of Embodiment According to Present Invention

Hereinafter, the outline of the embodiment according to the present invention will be explained. Then, the details of the configuration, the process, and the like according to this embodiment will be explained.

Regarding the data in the world, there are many instances where data can be accessed only in a way where personal information is not hidden from the aspect of personal information protection and the like. For example, for the medical-related data, unlinkable anonymizing might be performed by a method where the correspondence table between an individual person and the newly given symbol, number, or the like is not left such that this individual person cannot be specified. In the case of the unlinkable anonymizing, when some notification to a specific individual person is necessary as a result of data analysis, it is impossible to specify the target individual person. In the case of linkable anonymizing, it is necessary to specify the individual person using the correspondence table by a person (an attending physician or the like) who is permitted to access the personal information and it is impossible to perform massive and rapid notification to the individual person.

As a result of keen examination in view of the above-described circumstances, the inventors of this application developed a system that allows rapid and massive notification to a specific individual person based on a data analysis result while protecting the personal information. Specifically, this embodiment schematically has the following basic features.

That is, the data communication system according to this embodiment is configured such that a plurality of data analysis apparatuses, which each include a storage unit and a control unit, are communicatively coupled to one another. The storage unit of the data analysis apparatus includes a database that partially stores data that can be an access restriction target. For example, the database may store the information that allows specifying a notification target such as an individual person or the like.

The control unit of the data analysis apparatus according to this embodiment includes the data accessing unit that accesses a database at a given access level. Here, the data accessing unit may include a micromodule group that accesses the database at respective different access levels. The micromodule corresponding to the given access level functions.

The control unit of the data analysis apparatus according to this embodiment executes the application program based on the data acquired from the database via the data accessing unit to perform data analysis.

The control unit of the data analysis apparatus according to this embodiment performs communication control to allow transmission and reception of the data analysis result with respect to the other data analysis apparatus where the access level is different. Here, the other data analysis apparatus is the data analysis apparatus having the access level that is high to allow specifying the target such as an individual person, and may refer to the database based on the received data analysis result to specify the target and output notification.

Accordingly, this embodiment maintains the security not only for the medical information but also for highly-confidential information such as the information related to a compound itself, the living organism from which the compound is derived, and the genetic information coding the compound in a drug discovery process. Simultaneously, this embodiment provides the information in a disclosable part based on a certain condition to an outsider such as another department in a company, a research collaborator, and a cooperative company. This allows accelerating what is called open innovation.

That is, the disclosure to outside at a plurality of levels allows open innovation and development of an effective analysis method. The analysis result under the access restriction is taken over by the user having a secret level without access restriction. This allows performing analysis including undisclosable information and allows also specifying the notification target.

With the conventional method, it is necessary to reconfigure the analysis method developed outside on the system that allows the access to secret information. In the system according to this embodiment, as one example, common micromodule and program interface can be used to perform analysis without reconfiguration. Thus, the analysis of the outsider can be directly used. This allows protecting the secret information and allows the research with a research collaborator of a university or the like while, for example, allowing evaluation of a compound library and screening data of these compounds by the outsider as a potential client.

This allows evaluating the effectiveness of the compounds while protecting the secret information.

Thus, the explanation of the outline of this embodiment is ended.

Configuration of Data Communication System

Next, the detail of the configuration of the data communication system according to this embodiment will be explained below with reference to FIG. 1. FIG. 1 is a block diagram of an example of the configuration of the data communication system according to this embodiment, and conceptually depicts only the portion related to the present invention in this configuration.

As shown in FIG. 1, the data communication system according to this embodiment communicatively couples a plurality of data analysis apparatuses 100 to one another via a network 300. Here, in this embodiment, a terminal 200 such as a personal monitor device or an external device 600 such as an external analysis device other than the data analysis apparatus 100 may be coupled to the network 300. The network 300 has a function for coupling the data analysis apparatuses 100, the terminal 200, and the external device 600 to one another, and is, for example, the Internet or the like. Here, the following explanation refers to the configuration illustrated within a data analysis apparatus 100-1 in FIG. 1. Other data analysis apparatuses 100-2 to x are similarly configured.

As shown in FIG. 1, the data analysis apparatus 100 schematically includes a control unit 102 and a storage unit 106. The data analysis apparatus 100 may include an input unit (a keyboard and the like) and an output unit (a display and the like) (not shown). Here, the control unit 102 is a CPU or the like that integrally controls the overall data analysis apparatus 100. The storage unit 106 is a device that stores various databases, tables, and the like. These respective units of the data analysis apparatus 100 are communicatively coupled to one another via given communication paths. Further, this data analysis apparatus 100 is communicatively coupled to the network 300 via a communication device such as a router and a wired or wireless communication line such as an exclusive line.

The various databases and tables stored in the storage unit 106 are storage unit such as an immovable disk unit. For example, the storage unit 106 may store various programs, tables, files, databases, web pages, and the like used for various processes.

In these respective components of the storage unit 106, a database 106a is data storage unit that stores various data. Here, the data stored in the database 106a includes accessible data and data to which the access is restricted depending on an access level. For example, the data that can be an access restriction target is the information (the name, the date of birth, the address, the resident register code, the information for personal identification (the personal ID or the like), the mobile phone number, the comparison table that includes these pieces of information, and the like) that can specify an individual person or the like. In association with these pieces of information that can specify an individual person or any given dynamic ID, the database 106a may store medical information such as the medical record information, the drug prescription data, the medication intake data, and the health examination data of this individual person and the subjective symptom information and the behavior record data declared by the patient him/herself. The database 106a may store not only the medical information but also information such as the information related to a compound itself, the living organism from which the compound is derived, and the genetic information coding the compound in a drug discovery process. For example, the database 106a may store the protein structure information, the compound structure information, the compound library, the screening data of the compound for these pieces of information, the genetic information, the intermolecular interaction information, the protein structure similarity information, and the like.

These pieces of data might be accumulated in a large-scale database device or accumulated in a mobile device or the like possessed by an individual person. That is, the data analysis apparatus 100 may be configured as a large-scale database device such as a data server or configured as the device such as a mobile phone, a smart phone, and a monitor device. These pieces of data are stored in the database 106a. The control unit 102 of the data analysis apparatus 100 may download the latest data (for example, the medical information such as the medical record information, the drug prescription data, the medication intake data, and the health examination data of the individual person and the subjective symptom information and the behavior record data declared by the patient him/herself) from the terminal 200, the external device 600, and the like via the network 300 regularly and/or depending on the process by the control unit 102, to update the data stored in the database 106a.

As shown in FIG. 1, the control unit 102 has a control program such as an Operating System (OS), a program where various procedures and the like are specified, and an internal memory for storing necessary data. The control unit 102 performs information processing to execute various processes using these programs and the like. The control unit 102 functionally and conceptually includes a program executing unit 102a, a communication controlling unit 102b, a security controlling unit 102c, and a micromodule group 102m (a micromodule 102m1 to a micromodule 102mn).

In these units, the program executing unit 102a is a program executing unit that executes an application program based on the data acquired from the database 106a via the micromodule 102m. Here, the program executing unit 102a may execute the application program for performing data analysis to perform data analysis based on the acquired data from the database 106a via the micromodule 102m and acquire a data analysis result. The program executing unit 102a may reference the database 106a of this data analysis apparatus 100 (for example, the data analysis apparatus 100-1) and the data analysis result received from another data analysis apparatus 100 (for example, the data analysis apparatus 100-2) via the communication controlling unit 102b to perform data analysis (learning, meta-reasoning, or the like).

As the analysis method of the data analysis, various methods including known methods can be used. The program executing unit 102a may learn the analysis method. In the conventional technology, the method for increasing the accuracies of the individual analysis methods is common. Since there are: a data group that has a feature where the analysis accuracy is increased; and a data group where the accuracy is decreased in the respective methods, the respective analysis methods have different accuracies. Therefore, in this embodiment, the program executing unit 102a may execute a plurality of analysis methods in parallel using the data group where the result is known and learn which analysis method achieves the biggest increase in the total analysis accuracy in a certain situation.

Here, the program executing unit 102a may execute the application program in a master mode or in a slave mode. For example, during execution of the application in the master mode, the program executing unit 102a can cause the program executing units 102a of the other data analysis apparatuses 100 to function in the slave mode. In contrast, the program executing unit 102a can execute the application in the slave mode in response to the control from the program executing unit 102a of another data analysis apparatus 100 during execution in the master mode. The access level depends on the access level at the master side.

The program executing unit 102a may execute the application program for refining the notification to specify the notification target with reference to the database 106a via the micromodule 102m. For example, the program executing unit 102a may receive the data analysis result (a side-effect-risk-group identification analysis result or the like) via the communication controlling unit 102b from another data analysis apparatus 100 (for example, the data analysis apparatus 100-2) at a relatively low access level. Based on this data analysis result, the program executing unit 102a may refer to the database 106a of this data analysis apparatus 100 (for example, the data analysis apparatus 100-1) at a relatively high access level to specify the notification target and output a notification.

In the case of linkable anonymizing, the comparison table is held within the database 106a. Accordingly, the program executing unit 102a can acquire the ID dynamically generated from an external data analysis result to identify the individual person and the medical institution to which notification is required from the comparison table. When this method is used, it is possible to receive the data analysis result from the external device 600 (for example, an external security system of Intertrust Co., Ltd., Oracle Corporation, or the like) other than the data analysis apparatus 100 according to this embodiment and the program executing unit 102a of this data analysis apparatus 100 can notify a specific individual person and medical institution. However, this is limited to the case of linkable anonymizing and also requires checking using the dynamic ID. This process is a process with an especially high degree of secrecy and often requires the operation of the administrator with a special authority. Since this process cannot achieve unlinkable anonymizing, which is often used, another method may be used for the specifying operation as follows.

For example, if the presence of a high-risk patient is identified when analysis is performed using an anonymized database in the area with access restriction, it is necessary to perform the following process. The identical analysis is performed also from the inside of the medical institution where the database is not anonymized (for example, an organization without access restriction) so as to specify the patient identical to the patient specified by the analysis in the access restriction area. Accordingly, regarding the analysis process, the analysis processes within the access restriction area and the medical institution completely coincide with each other. To secure this condition, in each analysis process, the specified patient groups in the two processes need to always coincide with each other. To secure this condition, the program executing unit 102a may introduce a mechanism for checking the identity of the data record as the result of each process. For example, the program executing unit 102a may check the identity using a checksum method. As one example, the program executing unit 102a may process a specific area of the data record specified as an intermediate result of analysis using a predetermined calculating formula and check whether the intermediate results as the result of the two analysis processes coincide with each other. To avoid accidental coincidence between these checksums, the program executing unit 102a may introduce a plurality of checksums using a plurality of record items to significantly reduce the risk of the accidental coincidence.

The communication controlling unit 102b is a communication controlling unit that performs communication control between the data analysis apparatus 100 and the network 300 (or a communication device such as a router). For example, the communication controlling unit 102b performs communication control that allows transmitting and receiving the data analysis result acquired by the program executing unit 102a to and from another data analysis apparatus 100 at a different access level. As one example, the communication controlling unit 102b may function as an interface coupled to the communication control via a communication device (not shown) such as a router coupled to a communication line or the like. Here, the communication controlling unit 102b may have a function that performs communication of data via another device or the like such as the terminal 200 and the external device 600 and a communication line or the like other than the data analysis apparatus 100.

The security controlling unit 102c is a security controlling unit that controls the micromodule group 102m to perform access to the database 106a corresponding to the access level. For example, the security controlling unit 102c may cause the micromodule group 102m function corresponding to the access level to achieve the access corresponding to the access level. The security controlling unit 102c may query the database that stores the access level associated with any one or both of the application and the user to perform control that gives the access level corresponding to any one or both of the application and the user.

In this embodiment, the micromodule group 102m functions as a data accessing unit that accesses the database 106a at a given access level. Here, the micromodule 102m1 to the micromodule 102mn may access the database 106a at mutually different access levels. The functioning of the micromodule 102m corresponding to the given access level allows the access to the database 106a at this access level.

Here, in this embodiment, permission of the access to the database 106a at which level is determined mainly by the content of the application and the attribute of the user. For example, the information related to which level of the database 106a is allowed to be accessed when an application A is executed by a user X may be stored in a security database (not shown), for example, the storage unit 106 or the external device 600. Then, as a security control module (not shown) that controls execution of all the application on the database 106a, the security controlling unit 102c may query the security database about the application ID (APP-ID) and the user ID (UID) and consequently perform setting to activate the corresponding micromodule group 102m based on the given security level. The micromodule 102m that is not activated does not function.

This is an example of the configuration of the data analysis apparatus 100 according to this embodiment.

As shown in FIG. 1, the terminal 200 may have any one or both of: an external database that is mutually coupled to the data analysis apparatus 100 via the network 300 and stores various data; and a function that causes data input and notification output via an input unit 216 and an output unit 214, and the like. Here, the terminal 200 may be a monitor device possessed by an individual person such as a patient, a mobile device such as a mobile phone device and a smart phone, or the like. Here, the terminal 200 may transmit data to the database 106a of the data analysis apparatus 100 and receive notification information such as the data analysis result from the data analysis apparatus 100.

As shown in FIG. 1, the external device 600 may have a function for providing any one, some, or all of: an external program that performs data analysis or the like; an external database that stores various data like the database 106a; and a website on which a user interface or the like is executed, and the like. Here, the external device 600 may be configured as a WEB server, an ASP server, or the like. The hardware configuration of the external device 600 may be configured by an information processing device such as a workstation and a personal computer that is commercially available to the public and the accessory device of the information processing device. The respective functions of the external device 600 may be achieved by the CPU, the disk unit, the memory unit, the input device, the output device, the communication control device, and the like in the hardware configuration of the external device 600, the programs for controlling these members, and the like.

Process in Data Communication System

Figure 2:
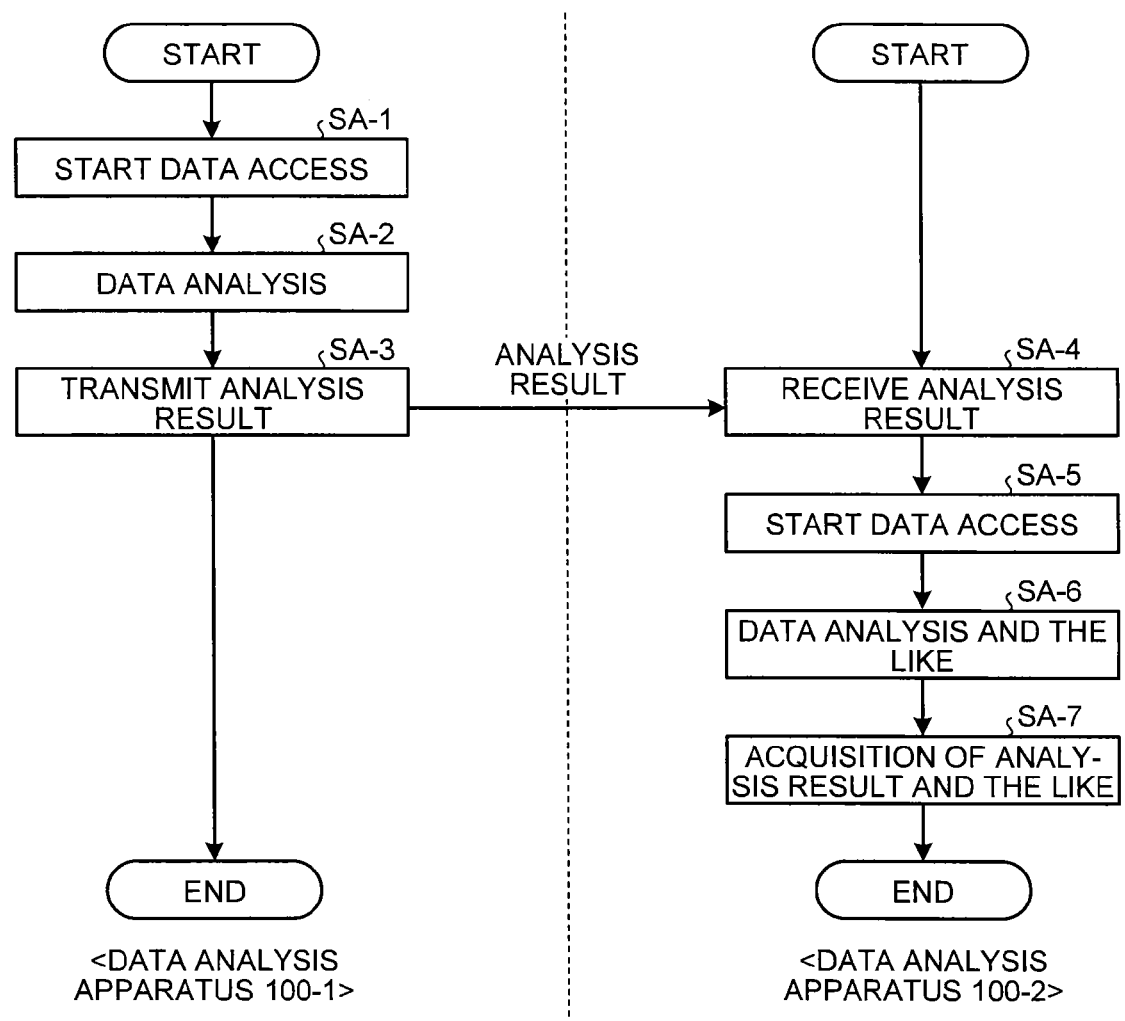
FIG. 2 is a flowchart of example of the process of a data analysis apparatus 100 according to this embodiment.

Next, the detail of the process in the data analysis apparatus 100 according to this embodiment thus configured will be explained below in detail with reference to FIG. 2 to FIG. 8. FIG. 2 is a flowchart of one example of the process in the data analysis apparatus 100 according to this embodiment. In the following example, an example of the process in the data analysis apparatus 100-1 and the data analysis apparatus 100-2 in the data communication system will be explained as an example. The data analysis apparatus 100 that performs the process is not limited to this example and may employ any configuration.

As shown in FIG. 2, the micromodule group 102m of the data analysis apparatus 100-1 starts the access to the database 106a at a given access level (step SA-1). For example, in the micromodule 102m1 to the micromodule 102mn, the micromodule 102m corresponding to the given access level may function to ensure the access to the database 106a at this access level. As one example, the access level is determined by the content of the application and the attribute of the user. Here, the security controlling unit 102c may perform setting to activate the corresponding micromodule group 102m based on the access level obtained by querying the security database about any one or both of the ID (APP-ID) of the application executed by the program executing unit 102a and the user ID (UID).

Subsequently, the program executing unit 102a of the data analysis apparatus 100-1 executes the application program for data analysis based on the data acquired from the database 106a via the micromodule 102m (step SA-2). The program executing unit 102a may execute the data analysis in association with learning, meta-reasoning, or the like.

Subsequently, the communication controlling unit 102b of the data analysis apparatus 100-1 transmits the data analysis result acquired by the program executing unit 102a to the data analysis apparatus 100-2 (step SA-3).

Subsequently, the communication controlling unit 102b of the data analysis apparatus 100-2 receives the data analysis result transmitted from the data analysis apparatus 100-1 (step SA-4).

Subsequently, the micromodule group 102m of the data analysis apparatus 100-2 starts the access to the database 106a at a given access level, similarly to step SA-1 (step SA-5).

Subsequently, the program executing unit 102a of the data analysis apparatus 100-2 executes the application programs for data analysis and the like based on the data analysis result received from the communication controlling unit 102b and the data acquired from the database 106a via the micromodule 102m (step SA-6). For example, the program executing unit 102a may reference the database 106a of this data analysis apparatus 100-2 to execute the data analysis such as learning and meta-reasoning in addition to the data analysis result received from the data analysis apparatus 100-1 via the communication controlling unit 102b. At this time, the program executing unit 102a of the data analysis apparatus 100-2 may execute the application in the slave mode in response to the control executed in the master mode by the program executing unit 102a of the data analysis apparatus 100-1.

The program executing unit 102a of the data analysis apparatus 100-2 does not only perform the data analysis but may also, for example, execute the application program for refining the notification to reference the database 106a via the micromodule 102m and specify the notification target. For example, the program executing unit 102a may refer to the database 106a of this data analysis apparatus 100-2 at a relatively high access level to specify the notification target and output a notification.

As above, the data analysis apparatus 100-2 acquires the data analysis result via a plurality of the data analysis apparatuses 100 at different access levels (step SA-7). The obtained data analysis result may be transmitted to a specified notification output party (the terminal 200 of a specified individual person or the like). In addition, the obtained data analysis result may be further transmitted to another data analysis apparatus 100 to repeat the above-described process.

As the conventional technology, to maintain the data security, there are a method (Derived Resources of Intertrust Co., Ltd., or the like) for dynamically generating a subset of the database and a method (Label Security of Oracle Corporation or the like) for controlling the access to the database using various security levels. These methods can hold the security of the database. However, a method that allows immediately providing information to an individual person or the primary physician from the analysis result. According to this embodiment, with sharing of the micromodules and application programs and cooperative processes, the analysis equivalent to the external analysis is performed inside where all the information can be accessed. Thus, it is possible to immediately make a notification reflecting the analysis result.

Thus, the explanation of the example of the process in the data communication system according to this embodiment is ended. Next, various embodiments of the configuration of the data communication system will be explained below.

(1) Configuration of System that Allows Integrated Analysis Using Database Across a Plurality of Organizations or the Like When a large amount of data is analyzed, it might be required to integrate and analyze data from a plurality of databases. In this case, conventionally, the configuration of distributed database is used to perform analysis on the premise that equivalent access is possible to any database and the consistency of the data or the like is ensured. However, since it is necessary to access a plurality of databases including medical information and the like but all the data cannot be freely accessed, it might be impossible to give equivalent access levels to the databases. Therefore, the data communication system according to this embodiment allows integrated analysis using a database across a plurality of organizations or the like. Here, FIG. 3 is a diagram of a system configuration example where databases across a plurality of organizations are integrated according to this embodiment.

Figure 3:
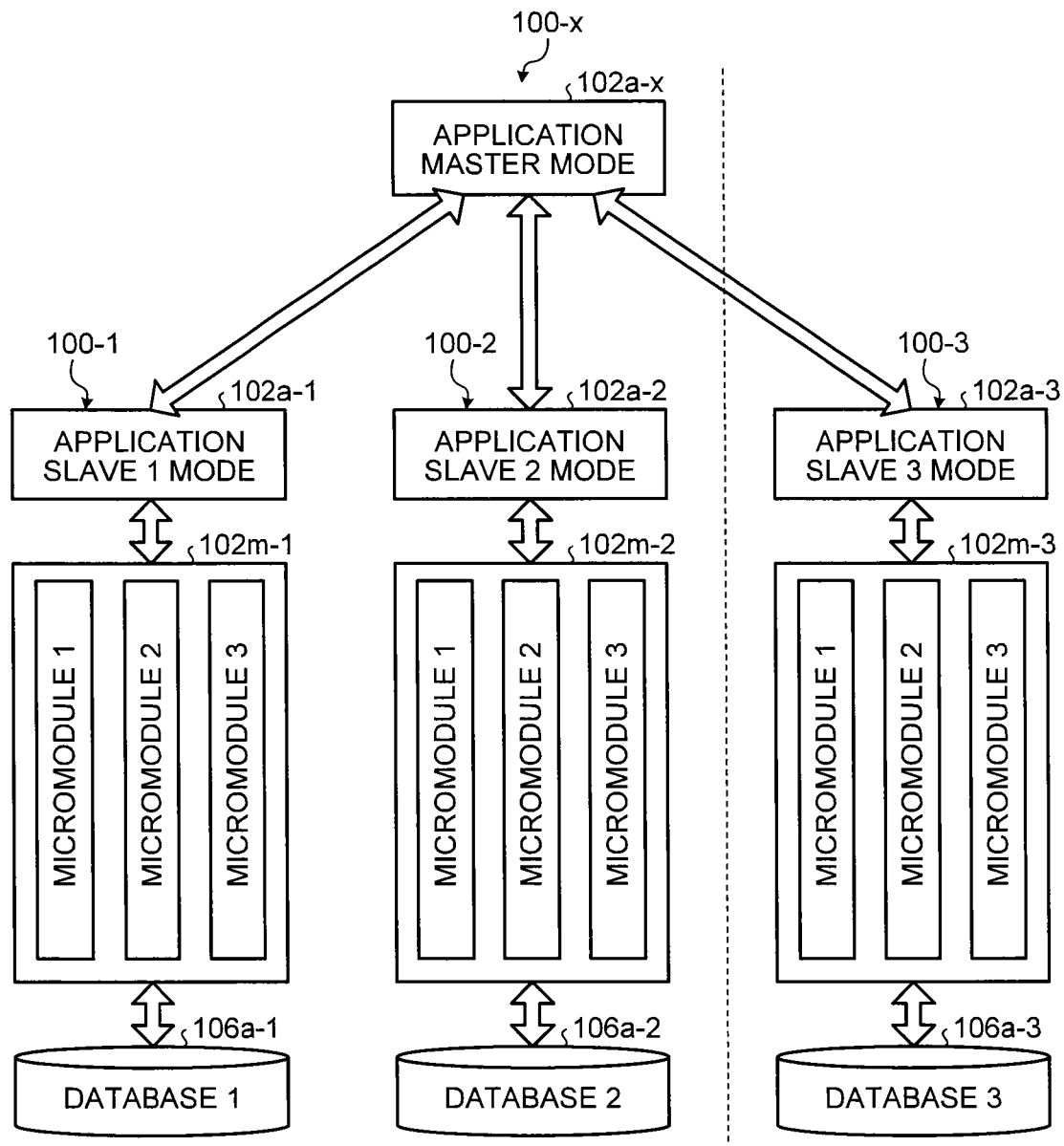
FIG. 3 is a diagram of a system configuration example where databases over a plurality of organizations are integrated according to this embodiment.

As shown in FIG. 3, the data communication system according to this embodiment has the following configuration. Micromodules 102m-1 to 3 that allow accessing and processing the data of respective databases 106a-1 to 3 are implemented with respect to the respective databases 106a-1 to 3. Application programs (102a-1 to 3) for performing intended analysis or the like proceed with analysis using these micromodules 102m-1 to 3.

Here, each database 106a may be a single database, a virtually integrated distributed database, or an aggregation of a plurality of databases. Furthermore, each micromodule 102m allows defining the access level preliminarily given to each database 106a, and this access level is dynamically determined by the access level of the module itself or the user during execution of the module.

For example, when the databases 106a-1 to 3 installed in different positions of A, B, and C are referenced, it is possible to perform the following setting. All the information of the database 106a installed in A is accessible in the data analysis apparatus 100 set to A. On the other hand, only restricted access is possible to the databases 106a-2 and 3 installed in B and C. In this case, it is possible to perform various settings of the restricted access, for example, setting where a part of the information in the databases 106a-2 and 3 in B and C is accessible, setting where only the result of the analysis on all the information by the micromodules 102m implemented on B and C is transmitted to A, and the like. This can be managed by setting at the slave side.

In the data analysis apparatus 100 as a local server that accesses each database 106a, the micromodule group 102m that allows wide range processes is implemented. Furthermore, an application program (102a) for performing a predetermined process using this micromodule group 102m is implemented. The application program (102a-x) operates in the master mode in the data analysis apparatus 100 operated by the user or a specified data analysis apparatus (for example, a data analysis apparatus 100-x in FIG. 3). When the application program (102a-x) operating in the master mode accesses the information of the databases 106a-1 to 3 that exist on the data communication system, the application programs (102a-1 to 3) implemented on the respective data analysis apparatuses 100-1 to 3 are started in the slave mode. Accordingly, these applications (102a-1 to 3) control the micromodule 102m to access the information and perform data analysis.

Between the program executing unit 102a, which executes the application, and the micromodule group 102m, and between the micromodule group 102m and the database 106a, the respective corresponding Application Programming Interface (API) groups may be defined. This API groups may be used to achieve access to the information.

The information accessible by the program executing unit 102a of each application and the information transmittable to the program executing unit 102a-x for the application launched in the master mode by the program executing units 102a-1 to 3 for the applications operating in the slave mode might be restricted by some factors such as the user and the server division. The mechanism for controlling this restriction can be achieved by a plurality of methods, and one of the methods is a method where a gatekeeper server is installed. In this method, while the program executing unit 102a-x in the master mode launches the programs (102a-1 to 3) in the slave mode or requests the respective processes of these programs, the permission level is requested from the slave side or the master side and the result of this request is responded to the slave side so as to determine the permission level. Without using the centralized control server, a similar control can also be achieved by keeping the information for determining the permission level in each server with distributed gatekeeper architecture and referencing this information.

(2) Configuration Via Another Data Security Method

Figure 4:
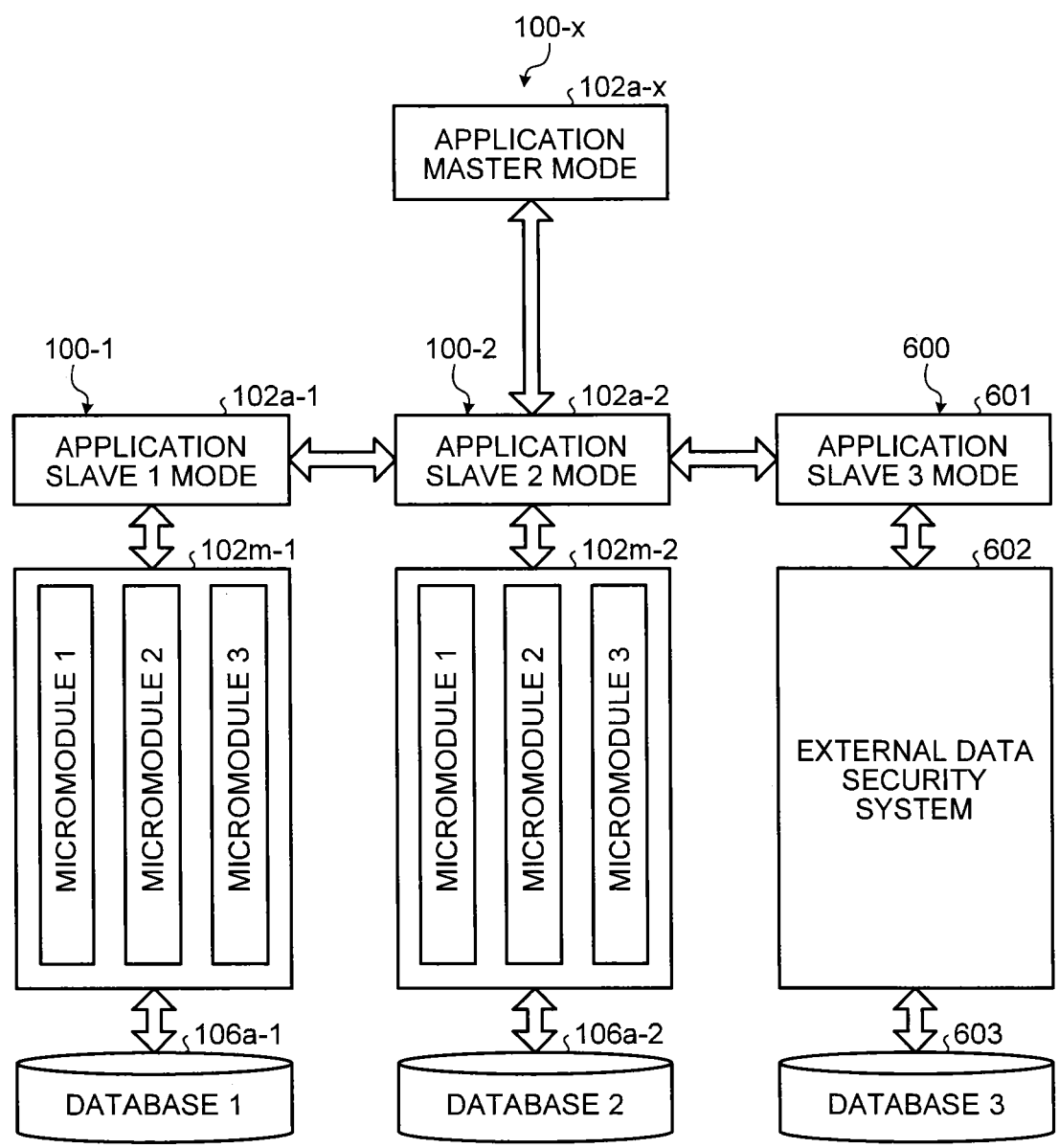
FIG. 4 is a diagram of a configuration example of the data communication system by replacement with an external device 600 as a data-security providing unit.

In the data communication system according to this embodiment, the micromodule group 102m and the database 106a can be replaced by another data-security providing unit. FIG. 4 is a diagram of a configuration example of the data communication system where the replacement by the external device 600 as the data-security providing unit is performed.

As shown in FIG. 4, the application program sets possible data access in the case of the master and in the case of the slave in compliance with the definition of the system providing the data security. As a result of the possible data access and internal processing, the process at the application side is performed. More specifically, in the example of FIG. 4, the external device 600 including an external data security system 602 in a database 603 is used. Further, the instruction to the programs of slaves 1 and 3 on the database 106a-1 and the database 603 and the information from these programs are transmitted to the program (102a-x) in the master mode via a slave 2. Also in this case, the consistent process is possible insofar as the process between the application program (102a-x) operating in the master mode and the application programs (102a-1 and 2 and 601) operating in the slave mode is clearly defined. Accordingly, when the external data security system such as the external device 600 is used, the information and the analysis result that are accessed from this external data security system are not identical. Execution of the application programs corresponding to the information and the analysis result in the slave mode allows efficiently integrating the data to the master program.

Furthermore, all the target databases do not always employ the identical data security system. A database with a plurality of data security systems, a database without using the external data security system, and the like might be mixed. Also when different data security levels are mixed, the configuration according to this embodiment ensures consistent data security and a more efficient process and allows maintaining the consistent analysis.

(3) Analysis Using Anonymized Medical, Health, and Behavior Information and Method of Information Notification for Individual Person The medical, health, and behavior data and the like are often used for analysis while the data are anonymized from the aspect of protecting the personal information. For the anonymizing, there are two types including: "linkable anonymizing" which allows identifying the individual person having each data under a certain procedure; and "unlinkable anonymizing" which does not allow the identification. When it becomes necessary to caution or alert an individual person in a group for a medical reason, the individual person cannot be immediately identified from the anonymized data and it is impossible appropriately and promptly caution or alert the individual person.

Therefore, in the configuration according to this embodiment, the micromodule group 102m and the application program (102a) whose operation has been tested are shared. The procedure identical to the analysis procedure that specifies the individual person to be cautioned is executed on non-anonymized data. This allows specifying the individual person identical to the individual person extracted by analysis using anonymized data and sending a notification to this person or a registered primary physician or attending physician. Here, FIG. 5 is a diagram of an example of the configuration according to this embodiment.

Figure 5:
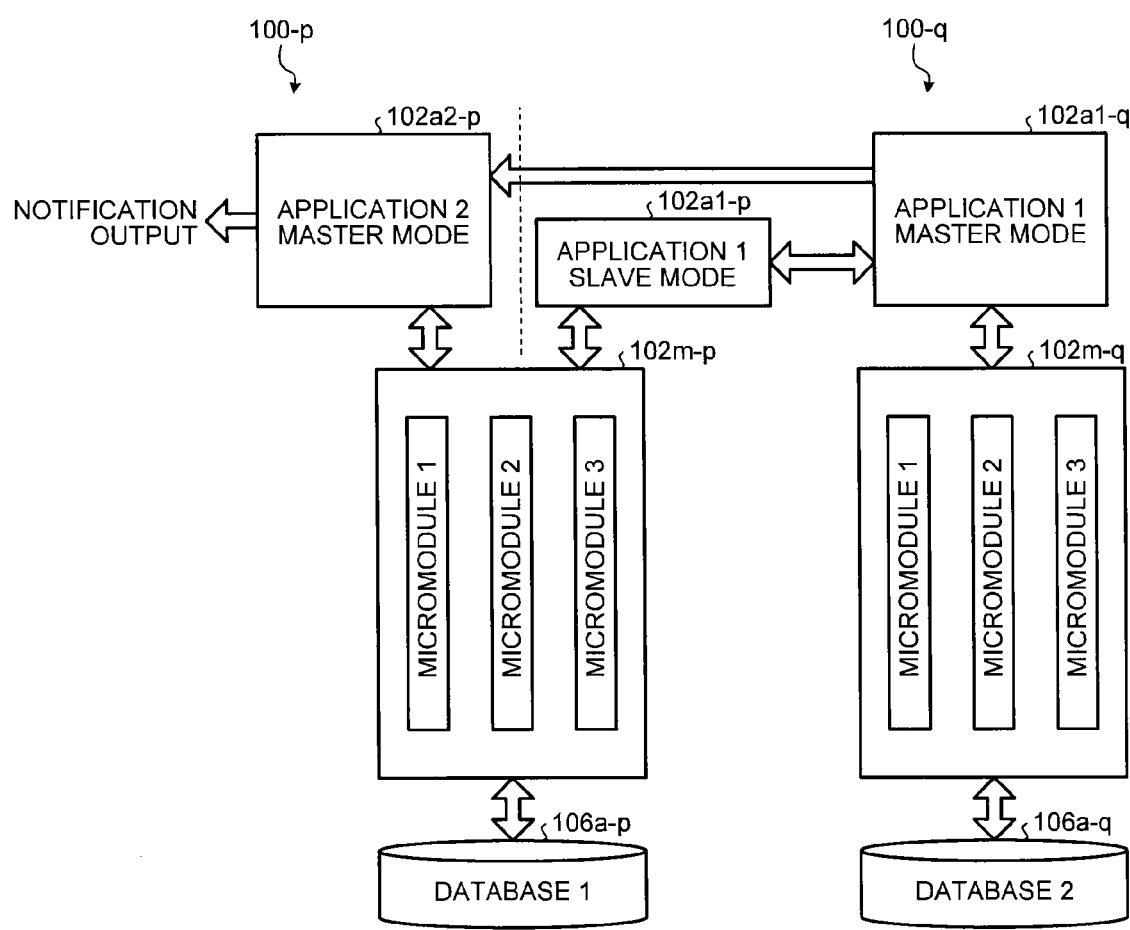
FIG. 5 is a diagram of an example of the configuration according to this embodiment.

As shown in FIG. 5, the application 1 is located in the access restriction area of a database 1 (106a-p). An application 1 starts the application (102a1-p) of a data analysis apparatus 100-p in the slave mode, extracts the individual person from the restriction information of the database 1 (106a-p), and notifies an application 2 (102a2-p) about the extraction procedure, a dynamic ID, or a part of the genome information. Because the access of a program executing unit 102a2-p of the application 2 is not restricted, the program executing unit 102a2-p can specify the individual person based on the received information and make a necessary notification.

When a linkable anonymizing process is performed, the comparison table or the like of the information that allows specifying the individual person, for example, the IDs, the individual names, and the like for each anonymized personal information is held. Accordingly, the application program 1, which performs analysis in the restricted section, can notify the application program 2, which operates within the accessible section, about the personal information ID to specify the individual person using the comparison table or the like. Here, FIG. 6 is a diagram for an instance where there is an access restriction on the common database 106a-1.

Figure 6:
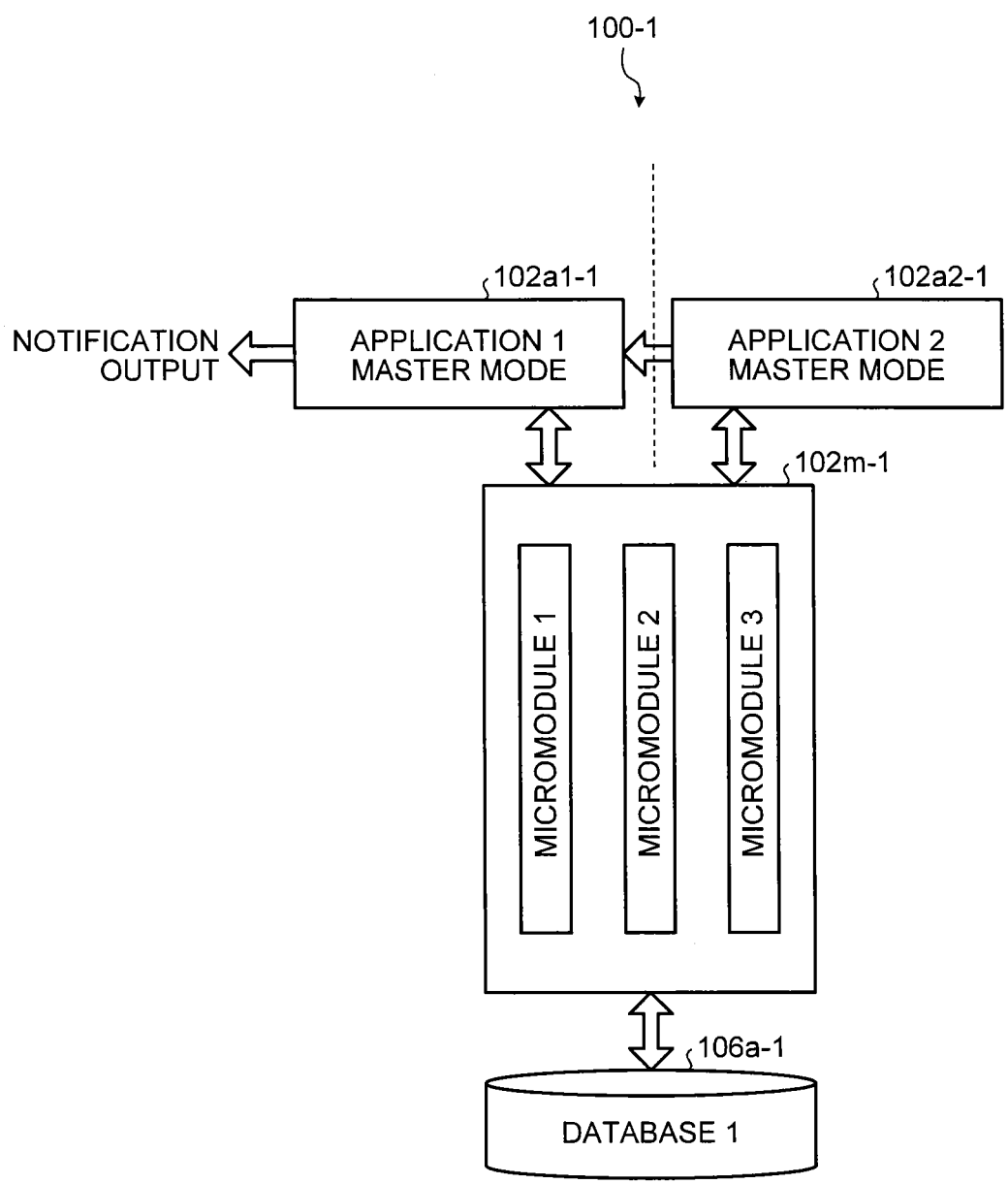
FIG. 6 is a diagram when there is an access restriction on a common database 106a-1.
Figure 7:
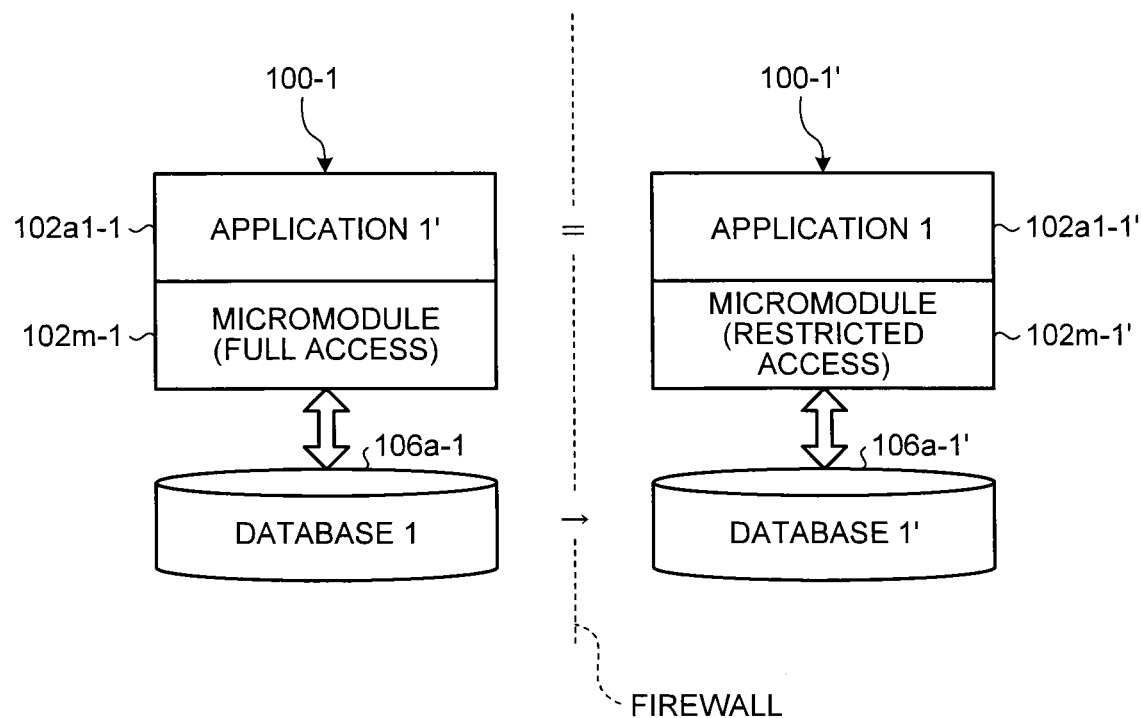
FIG. 7 is a diagram of an implementation where a copy 106a-1' as the anonymized database 106a-1 is generated and the copy can be analyzed outside of a firewall.

As shown in FIG. 6, a program executing unit 102a2-1 of the application 2 in the restricted section transmits partial information of gene sequences and the like of the extracted individual person as a virtual ID to a program executing unit 102a1-1 of the application 1 within the accessible section. The program executing unit 102a1-1 of the program 1 within the accessible section specifies the individual person matching these pieces of information. This allows announcement of the information to the individual person, the attending physician, or the like. In this case, the application 1 and the application 2 have different combinations in the micromodule group 102m-1 to function for controlling execution or non-execution of the access restriction. This example should not be construed in a limiting sense. The mirrored database and the like may be used. FIG. 7 is a diagram of an implementation where a copy 106a-1' as the anonymized database 106a-1 is generated and the copy can be analyzed outside of a firewall. In this example, the access level (full access, restricted access, or the like) can be set for each micromodule 102m attached to the data analysis apparatus 100.

The user who performs analysis might not be a doctor or the like who has full access authority. Also in this case, the application for analysis (the application 2 in FIG. 6, the application 1 in FIG. 7, or the like) and the application for notification (the application 1 in FIG. 6, the application 1' in FIG. 7, or the like) can be implemented with respect to the identical database to make a notification to a specific individual person while performing analysis using anonymized data. The database need not be limited to a database installed on a medical institution or the like, and may be a personal server, a cloud server, furthermore, a measurement device or a mobile phone possessed by an individual person, or the like.

In this embodiment, each micromodule 102m employs the micromodule 102m with security protection. Accordingly, even when the application is attacked, it is necessary to individually remove the securities of the respective micromodules 102m. Thus, if the security of one micromodule 102m is removed, not all the information becomes accessible. That is, there is an advantage that even if only the information accessible by the respective micromodules 102m suffers damage, not all the data immediately suffers damage.

Configuration and Function of Analysis/Inference Engine

Figure 8:
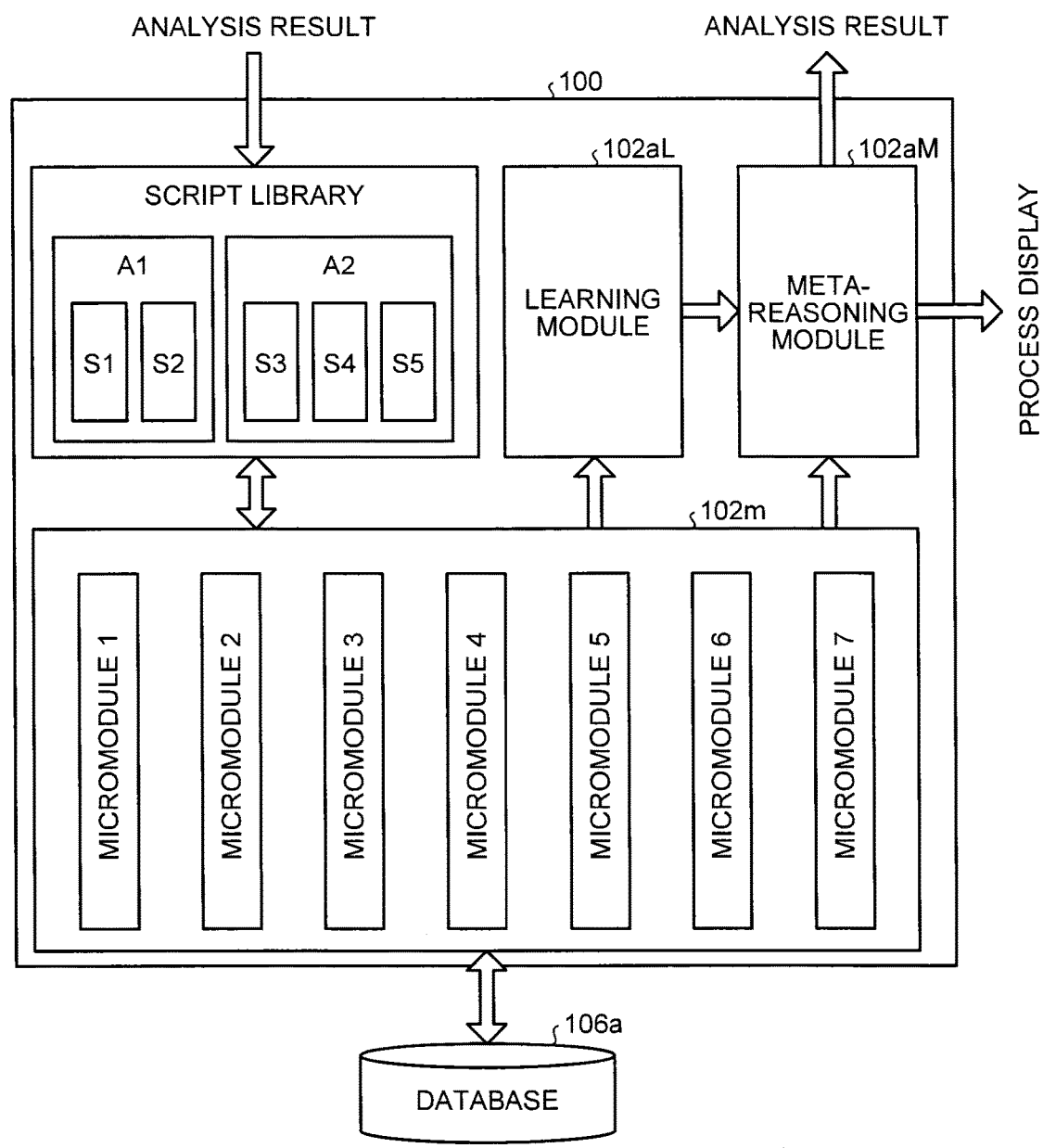
FIG. 8 is a diagram of the functional configuration of the data analysis apparatus 100 that includes an analysis/inference engine.

Next, examples of the configuration and the function of an analysis/inference engine that functions by execution of the application for data analysis by the program executing unit 102a will be explained. FIG. 8 is a diagram of the functional configuration of the data analysis apparatus 100 that includes the analysis/inference engine.

As shown in FIG. 8, in the analysis/inference engine (a learning module 102aL, a meta-reasoning module 102aM, and the like), multiple individual analysis and inference algorithms are implemented. The group of these algorithms is executed by a sequence of separately defined scripts or a program where the procedure is defined. There might be a plurality of different scripts for the identical analysis/inference. In this case, the respective scripts are executed at the identical level unless otherwise instructed separately. It is possible to preliminarily get how to obtain the final result where the accuracies of the respective script and the respective analysis/inference results are summed up, using a method such as machine learning based on a sequence of tests executed using verifiable instances.

It is possible to employ "event-driven anomaly detection" where analysis is started based on the occurrence of a specific event as the timing for starting analysis. For example, when the user inputs a specific event such as physical abnormality via the input unit 216 of the terminal 200 or when the terminal 200 for measurement detects the abnormality, the data analysis apparatus 100 may start analysis based on this event. Based on the information of a specific individual person, it is possible to perform analysis corresponding to this individual person. When events in a certain group are accumulated, it is possible to start analysis on the entire group.

Here, the program executing unit 102a can use the following method as an analysis method using genetic information.

(1) Genome Wide Association Study (GWAS)

(2) Conditional Genome-Wide Association Study (conditional GWAS): Because a specific genetic polymorphism might not affect the representation system unless under a specific condition, simply performing GWAS analysis does not allow capturing the influence of the genetic polymorphism. Here, the conditional GWAS where GWAS is performed under a specific environmental condition is implemented.

(3) Genome-Wide Network-based Association Study (GNAS): While the GWAS method is used for analysis, a gene regulatory network is used to specify the gene group to be noticed and preliminarily limit the analysis range.

(4) Conditional GNAS: GNAS is performed under a specific condition to increase the accuracy and the efficiency of analysis on the genetic polymorphism that is coupled to the representation system only under the specific condition.

With this configuration of the analysis/inference engine, the data analysis apparatus 100 can analyze a group using, for example, the taking pattern, the health data, and the behavior data of patients who take a certain medication based on the self-reported data stored in the database 106a or the diagnostic data from a medical institution to detect whether a behavioral anomaly in taking the medication might occur. Furthermore, performing analysis additionally using gene information allows determining whether a specific side effect and the problem and the effect of the taking pattern are caused by a specific genetic background.

EXAMPLES

Examples of the data communication system according to this embodiment will be explained. As one example, this Example relates to a data communication system as follows. The data communication system accumulates massive and various databases and the data that is updated as necessary and grows. Simultaneously, the data communication system executes a plurality of methods for analyzing these pieces of data under the condition where various restrictions are imposed on the data access, generates a hypothesis based the data, has functions such as notification of individual analysis results or the like, and helps the determination of the user using these functions.

It is an object of this Example is, as one example, to: perform early detection of a specific side effect; predict the effect in a clinical trial; and detect and analyze the health abnormality due to taking a medicine in a deviant manner or reduction in medicinal effect, using personal genome information related to management for taking a medicine, genetic polymorphisms, and the like; and to analyze the effect of a medicine after being released to the market. As one example, this Example is configured to be used when health-related information widely including the gene information of an individual person is analyzed and the result of the analysis is notified. As the background of the development of this embodiment, there are conventionally the following problems.

It is an important medical problem to analyze the effect and the side effect of the medicine after being released to the market. Particularly, in a clinical trial, there might be occurrences of: the unexpected side effect or effect in the patient having a genetic background that has not been encountered yet; and the enhancement of the effect or the side effect due to the unexpected synergistic effect with another medicine; and the like. When an unexpected side effect uncommonly occurs, the medicine might be required to be withdrawn from the market. In this case, when the side effect is found late, the pharmaceutical company or the pharmaceutical authority faces a risk for paying hefty settlement.

Whether the medicine is appropriately prescribed or further appropriately taken is a major factor to understand the effectiveness, the side effect, and the like of the medical practice. Monitoring of taking a medicine allows finding inappropriate prescription, taking, and the like and also allows introducing the measure for prompting an appropriate dose. Promptly finding that the problem occurring on the patient is the problem related to an appropriate dose of medicine is important to prompt an appropriate dose and achieve the relief of the symptom.

Furthermore, when a medical decision is made, it is important to analyze treatment information such as an extremely large amount of medical records and establish an appropriate treatment strategy. To do so, it is necessary to integrally access and analyze the medical records and the related treatment information of a plurality of medical institutions. However, these pieces of information are personal information where a certain restriction is imposed on the access from outside.

It is an object of this Example to allow analyzing the data of the medical institutions while maintaining this restriction so as to prompt quicker and more accurate establishment of the treatment strategy. Furthermore, when it is necessary to caution a patient or the attending physician of the patient for a medical reason or notify information to them, an outside analyst needs the mechanism where a notification is accurately arrived for a target patient or the attending physician of the target patient without specifying the personal information. Since a new knowledge comes from the analysis on the personal genetic information, it is an object of this Example to notify the result to the related individual person, the attending physician of the individual person, and the like so as to allow utilizing this result for the prevention of the disease, the prevention of the side effect due to dose, planning of a more effective treatment strategy. That is, it is possible to provide the data communication system where the analyst can notify a necessary individual person without having the information for specifying the individual person.

Simultaneously, the analysis method for these data is on the way of research and development. A new method is continuously produced. Furthermore, the collectable data changes according to the technical progress, the change of perception of the user, and the change of the social system. In this Example, the areas at different access levels can be analyzed in a cross-sectoral manner. Accordingly, adding personal behavior information or the like to the analysis of these areas allows a more exhaustive and continuous analysis. This might be associated with improvement in personal health or medical care quality. That is, this embodiment relates to the configuration of the system that continuously allows analysis, evaluation, and verification of hypothesis for the data under these environments that continuously change. This embodiment is the mechanism that allows a wide variety of applications including analysis of the economic data and the like other than Examples described below.

Examples of the data communication system according to this embodiment will be explained below with reference to FIG. 9 to FIG. 18.

First Example

Figure 9:
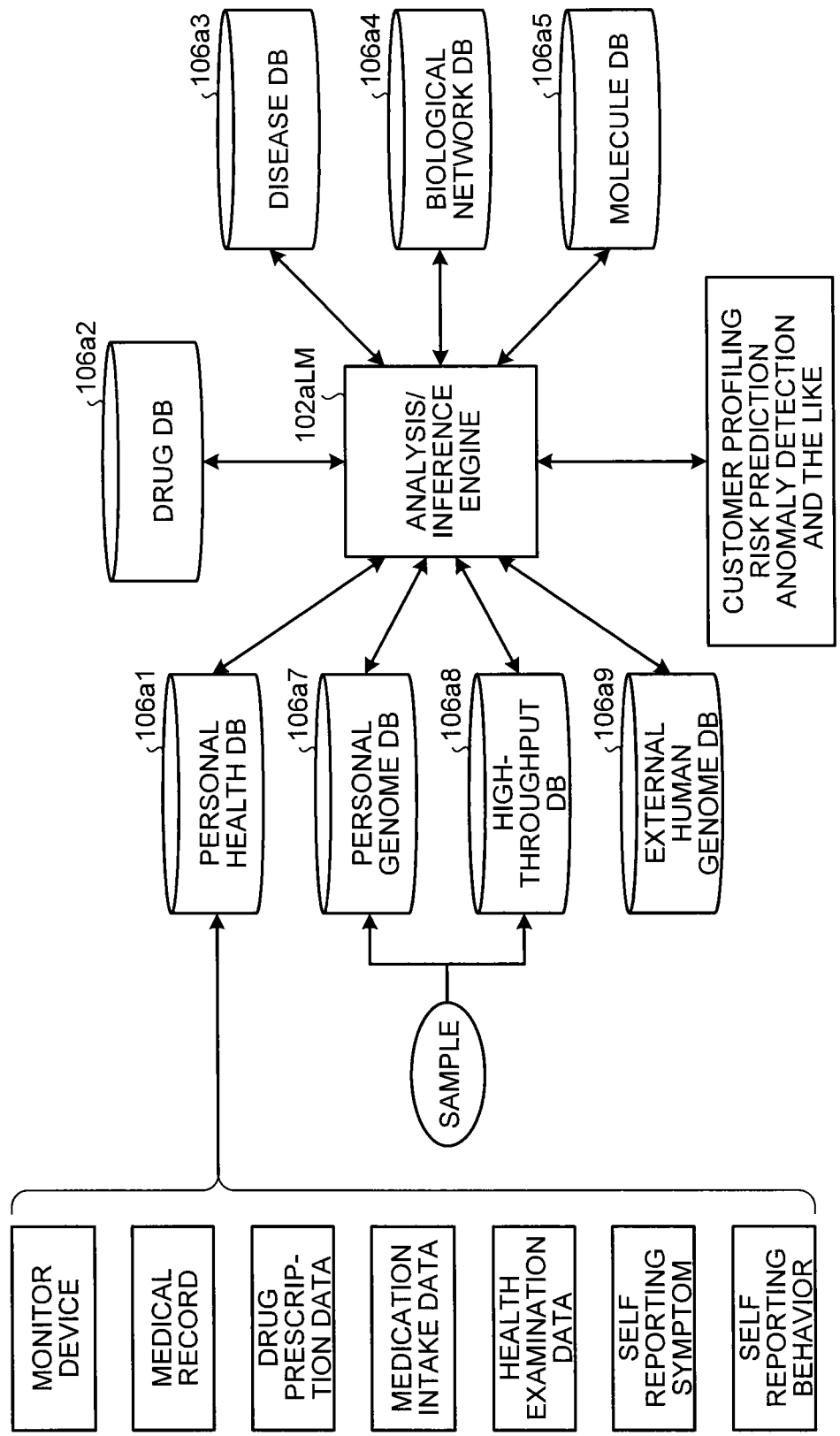
FIG. 9 is a diagram of an example of the configuration of a data communication system in First Example.

First Example relates to early detection of the side effect of a medicine after being released to the market and optimization of a taking pattern. FIG. 9 is a diagram of an example of the configuration of the data communication system according to First Example.

As shown in FIG. 9, this data communication system as one embodiment is constituted of: a plurality of databases 106a1 to 9; interfaces coupled to a plurality of data acquiring devices; a plurality of analysis modules; a storage device that accumulates a program group for controlling these members and analysis results; a device that checks the analysis result against the demonstration result; a meta-reasoning part 102aM that derives the optimal estimation from the output of the analysis module group; a learning module part 102aL that generates various parameters of the meta-reasoning part and rules; a database for back test; and a device that establishes the database for back test from a master database.

There are multiple instruments for measuring the data (the medical record information, the drug prescription data, the medication intake data, and the health examination data of an individual person, the subjective symptom information and the behavior record data declared by the patient him/herself, and the like) related to a personal health status. These instruments as the terminal 200 transmit the measurement results to the data analysis apparatus 100 as a server via the network 300 or the like to accumulate the measurement results in the personal health database 106a1. The individual person can input the measurement results of these instruments from the input unit 216 via software or the like. This input includes the case of manual input from a computer or a mobile terminal and the case where the measurement-result display screen of the instrument is photographed and the data digitalized from the image data through an image analysis device is accumulated in the data analysis apparatus 100 as the server. Furthermore, the data such as the inspection result of the hospital or the medical examination can be accumulated in the data analysis apparatus 100 as the server online or can be input using a method of a manual input, scanning, imaging, or the like by the individual person to be accumulated in the server.

Furthermore, based on the extracted sample of the individual person, genome analysis (whole-genome analysis, exon sequence analysis, or the like) may be performed to accumulate the result in the personal genome database 106a7. At this time, the data analysis apparatus 100 may perform epigenome analysis.

Furthermore, the data analysis apparatus 100 may analyze the metabolic profile (metabolome data), the transcriptional expression data, or the epigenome from the sample of the individual person extracted regularly or as necessary to accumulate the analysis result in a high-throughput database 106a8.

As shown in FIG. 9, a drug database (Drug DB) 106a2 accumulates various information related to medicines. This information includes the chemical formula, the molecular structure, the binding region, various chemical activity data, the target molecular data, the side effect data, the target illness, the standard protocol for each target illness, and the like, regarding medicines. The drug database 106a2 may include an adverse events database (Adverse Events DB).

The adverse events database is a database where the reports of the events considered as side effects are accumulated. This database includes either or both of the accumulation of unique reports and the accumulation by analysis from the database of a regulatory authority such as Food and Drug Administration (FDA).

A disease database (Disease DB) 106a3 is a database related to various diseases. Here, regarding various diseases, the causative gene, the candidate causative gene, the related-genetic-polymorphism information, the numerical range of the biological information reflecting the stage of disease, the information related to qualitative and quantitative symptoms, the information related to the standard treatment, and the like are accumulated.

A biological network database (Biological Network DB) 106a4 accumulates interaction networks such as a gene regulatory network and an intermolecular interaction network.

A molecule database (Molecule DB) 106a5 accumulates information related to a biomolecule. This information includes the molecular weight, the structure, the sequence information, the interaction information, the binding constant, the separation constant, and the like.

In these databases, access restrictions might be imposed on the personal health database 106a1 related to the health information of the individual person, the personal genome database 106a7 related to the gene information of the individual person, the data storage on the device used by the individual person, and the like. Accordingly, it might be necessary to execute the analysis application in the slave mode with access restriction. This is executed using the mechanism according to this embodiment. These databases 106a might be distributed to be held on a plurality of medical institutions or a related cloud service. It is necessary to implement the consistent micromodule group 102m and application program (102a) on these databases.

Based on these pieces of information, an analysis/inference engine (classifier & inference engine) 102aLM detects a specific side effect due to a medicine, detects an abnormal medicine-taking pattern, predicts the personal disease risk, and analyzes the effect and the side effect of the medicine after being released to the market (see the configuration of the analysis/inference engine 102aLM in FIG. 8).

Furthermore, the analysis/inference engine 102aLM provides the analysis result/data required for predicting the medicinal effect and the side effect of the candidate compound before the clinical trial and during the clinical trial to a medicinal-effect/side-effect prediction system that is separately configured.

Furthermore, the information of the patient group who take a specific medicine, the gene information, the already-known medical, and biological data can be used to instantaneously identify the side effect and the like of the medicine and further specify the causative factor (the genetic factor, the environmental factor, and interaction between a plurality of medicines). The method necessary for these analysis is realized by each analysis module or a combination of these analysis modules. For each development of new methods, modules or the like where these methods are implemented are added.

Respective different sets of the databases 106a in the database group 106a1 to 9 may be used for different applications. The application of the security method according to this embodiment to the access to these databases 106a and the use of the learning algorithm by the simultaneous parallel execution and the meta-reasoning system based on the learning result for the inference engine are consistent.

The personal health database 106a1 records respective pieces of the information related to personal health collected by various methods. In the case of medical charts, the anamnesis, the medication history, the diagnosis history, and the like are described. Drug prescription data is the medication history and the prescription information. From the terminal 200 of the monitor device, actual medicine-taking information and the like are collected in the personal health database 106a1. Here, FIG. 10 is a schematic diagram of the procedure in the process for analyzing a side-effect risk group based on the personal health database 106a1.

Figure 10:
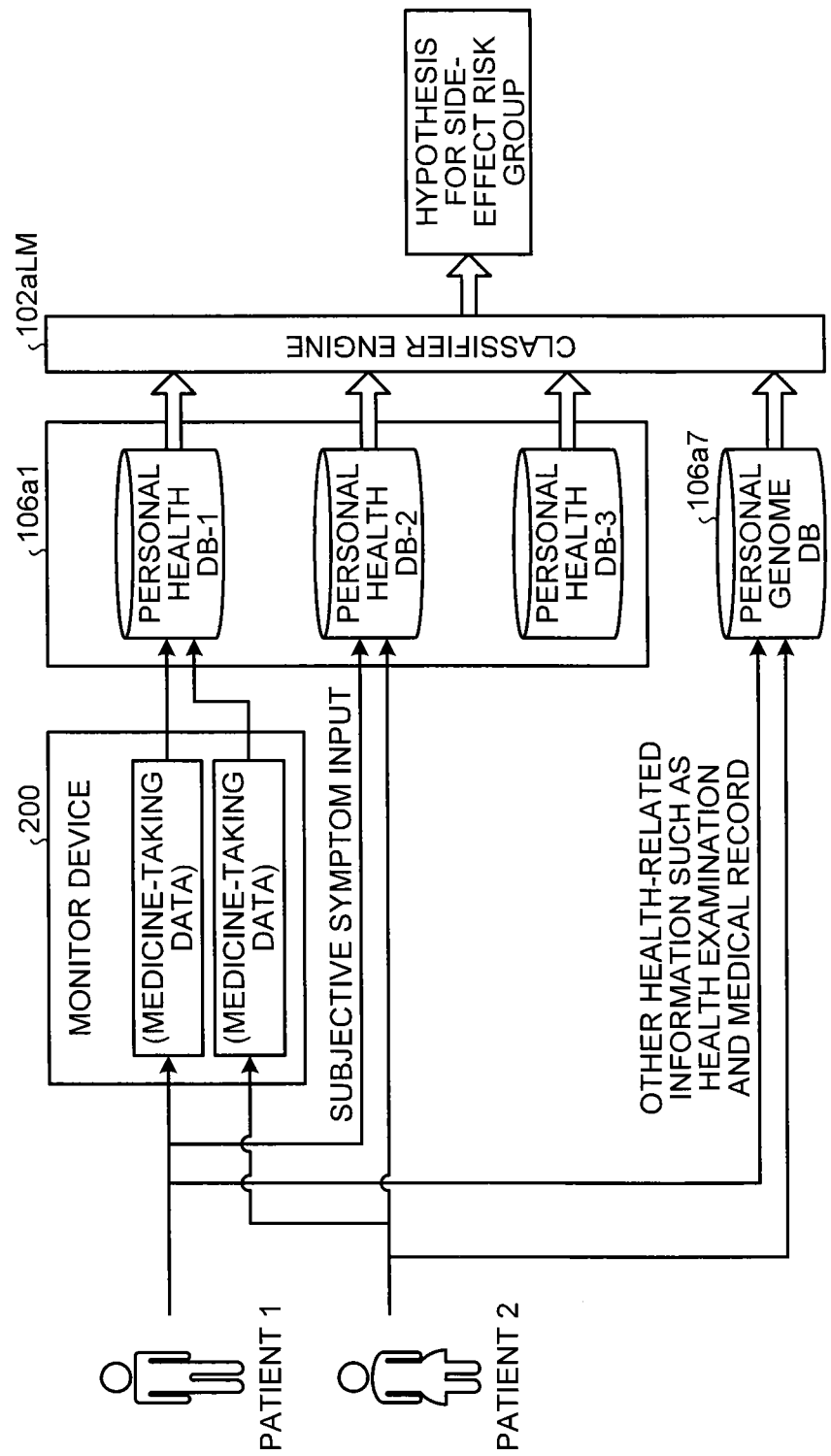
FIG. 10 is a schematic diagram of the procedure in a process for analyzing a side-effect risk group based on a personal health database 106a1.

As shown in FIG. 10, for example, assume that a patient 1 daily takes a medicine A from one day on suspicion of an illness of X. From the monitor device, the name, the dosage, the taking time, and the like of the medicine are transmitted. Assume that this patient complains of a palpitation after two weeks from the start of dosing. At this time, the date and time when the palpitation is felt, the strength of the palpitation, and the like are reported by a method of self-reporting symptoms, this report is recorded in a personal health database 106a1-2. Furthermore, the gene information or the like of the individual person is recorded in the personal genome database 106a7. Here, assume that it is reported that there is a risk for an irregular heartbeat, a palpitation, and the like when a gene of H has a specific genotype.

In this case, to examine whether the medicine A causes the irregular heartbeat and the palpitation to this patient group, the analysis/inference engine 102aLM searches the patient group who take the medicine A and where the palpitation and the irregular heartbeat are reported. Therefore, the analysis/inference engine 102aLM and the data analysis apparatus 100 calculate whether the occurrence frequencies of symptoms of the palpitation and the irregular heartbeat are significantly different between: the patient group where the gene of H has the specific genotype; and the patient group that has another genotype, or the like.

Here, if the statistical significance is established, the medicine A is considered to be an incentive for the palpitation and the irregular heartbeat with respect to this specific group. Furthermore, as the next step, it is effective to actually communicate to a patient or an attending physician of the patient that this patient takes the medicine A and has a risk due to a specific genetic form of the patient. Here, unlinkable anonymizing is performed on the database that accumulates the patient information used for analysis and on the analyst. Here, FIG. 11 is a schematic diagram of the procedure in the process for refining a medical-information notified party.

Figure 11:
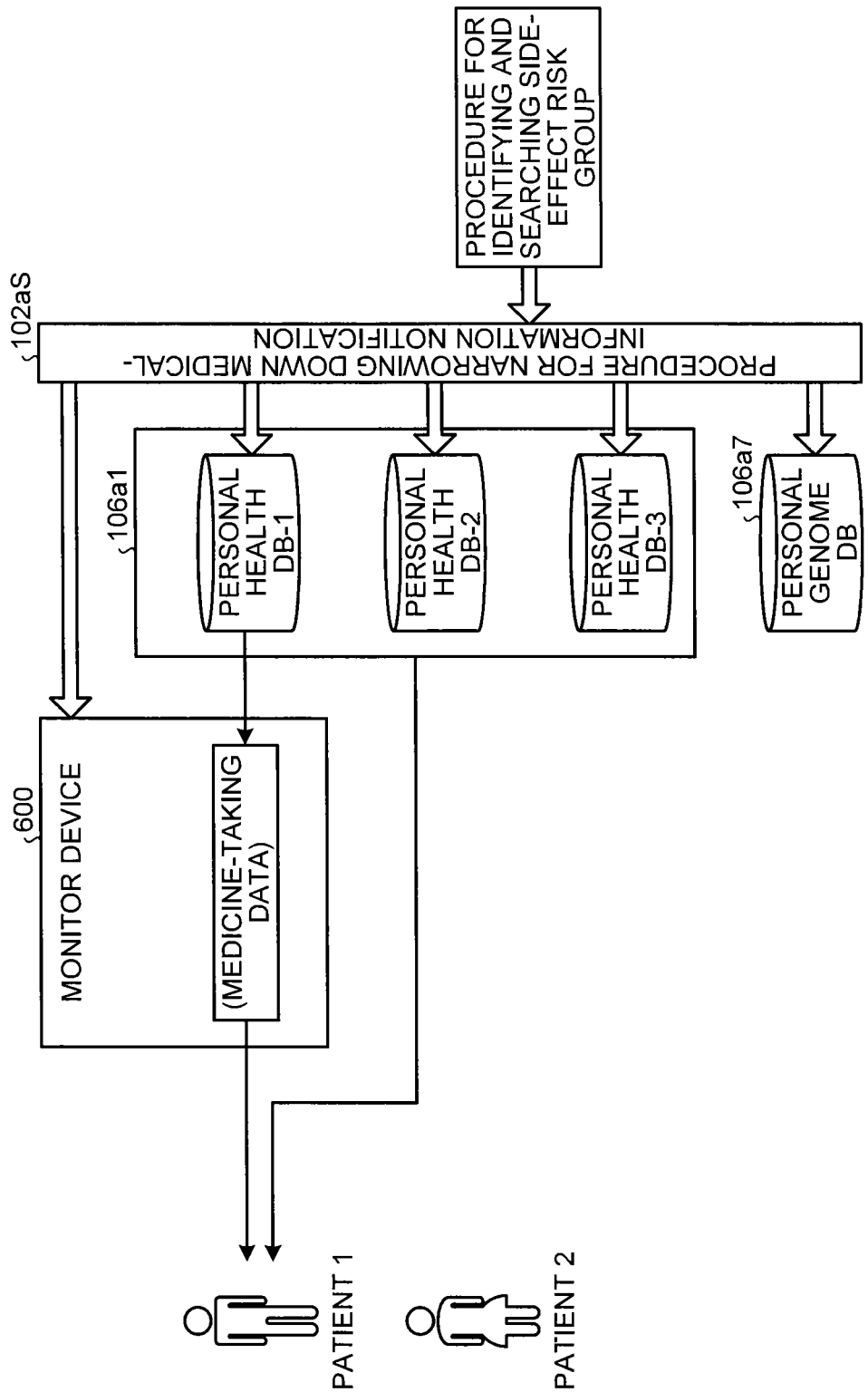
FIG. 11 is a schematic diagram of the procedure in a process of a procedure for refining a medical-information notified party.

As shown in FIG. 11, based on the login or the like of the user such as an access administrator, a program executing unit 102aS that executes the application for refining the notification executes a sequence of procedures that has found a specific high-risk group on the original database. As the result, the patient identical to the patient narrowed down by the analysis must be emerged as the high-risk group. In this database, the information for specifying an individual patient and the information related to the attending physician of the patient are also recorded. Accordingly, this information is used to report the medical risk to the patient him/herself or the attending physician. At this time, it is possible to notify not all the patients who take the medicine A but only the patient having the specific risk.

It is possible that the correlation between the side effect of the medicine, the genetic background, and the like is not known. In such a case, a refinement application (102aS) specifies the phenomenon to be focused on from the data of the subjective symptom, the medical record information, the health examination information, and the like. For each genetic variation to be focused on, the refinement application analyzes whether the side effect focused on in the group who take the medicine significantly occurs or the like, using various statistical analysis methods (see FIG. 11). At this time, based on the gene of the group having a significant risk of the side effect and the genotype of this gene, the biological network database 106a4 is used to confirm whether the gene has a direct or indirect interaction with the gene group associated with the side effect. Accordingly, the molecular mechanism behind the statistical significance can be explained (see FIG. 9).

This analysis uses an extremely wide variety of databases such as the abnormality, the gene, and the type of the medicine to be noticed, and a certain formulaic analysis method is not determined. Therefore, this communication control system allows testing various analysis procedures and simultaneously using the method of machine learning or the like to learn that which method of these methods is more effective in which state or the like and allows selecting the most appropriate method for individual analyses on a wide variety of phenomena to use this result. For example, the procedures of the analysis are assumed to be defined from A1 to A10 (see FIG. 8). However, for the respective procedures, the correlations between the side effect, the medicine, the genotype, and the like can be actually detected with high accuracy under mutually different specific conditions. It is not clear that which method is the most effective under which condition. In this method, a plurality of instances where the correlative relationship has been already demonstrated is used to execute these methods in parallel. The result is mechanically learned using the demonstrated data. The use of this result causes automatic selection of the analysis method considered to have the highest accuracy for the specific condition and allows presenting the analysis result to the user.

Second Example

According to this embodiment, Second Example related to the system for prompting an appropriate dose of medicine will be explained below.

Firstly, the background of the configuration of the system in this Second Example will be explained. The information of the personal and medical devices for recording the prescription and the dose of the medicine are recorded in the devices themselves or the database coupled to these devices. Furthermore, there is a database that records the state and the behavior of the patient and the like. Necessary information is automatically or manually recorded in this database. For example, if the medicine is not taken for some reason, when there are a certain percentage of patients whose symptoms get worse at a certain rate, strict dose management for all the patients is not effective and accurate dose management for the patient requiring a strict dose is desired.

It is possible to extract which patient requiring strict dose management and occurrence of the state without dosing by analyzing the database 106a where the medicine-taking information and the state-behavior information of the patient are recorded. Here, the gene information might also be referenced as necessary. These pieces of information are personal information, and need to be anonymized to be used for analysis when a large-scale analysis is performed collectively on the information.

This anonymized data is provided to the large-scale analysis in conjunction with the dose-management application for the target disease. As a result, it is possible to obtain the analysis result that the patient having which feature is appropriate to be the target for the strict dose management. However, in this case, the provided data is the anonymized data and which specific patient as the target of the dose management is unknown by the provided data as it is. Depending on the illness, it might be preferred to strictly protect the personal information. As an assumed anonymizing method, unlinkable anonymizing is used and the data is provided to an analyst. In this case, it is impossible to specify the individual person and appropriate information cannot be provided to the necessary individual person or the attending physician of this individual person.

In the system according to this Second Example, the process identical to that used in the analysis procedure is executed on the personal terminal to which the information is provided or the cloud that is coupled to the personal terminal and accumulates the data. As a result, a necessary message is displayed for the terminal determined that notification is necessity. In this case, the patient or the attending physician of this patient can understand that strict dose management is necessary.

Furthermore, recording the dose information in the terminal and the database in real time allows analyzing forgetting of dose or an inappropriate taking pattern in real time. For example, the database is checked at regular intervals such as every hour and every six hours to check the allowed disturbance in the taking pattern for each patient. Here, when the deviation from the allowable pattern is found, it is possible to immediately make a notification for prompting a dose. This checking of the taking pattern can be executed on the respective databases and the device after the deviation criteria are defined from the analysis application.

Figure 12:
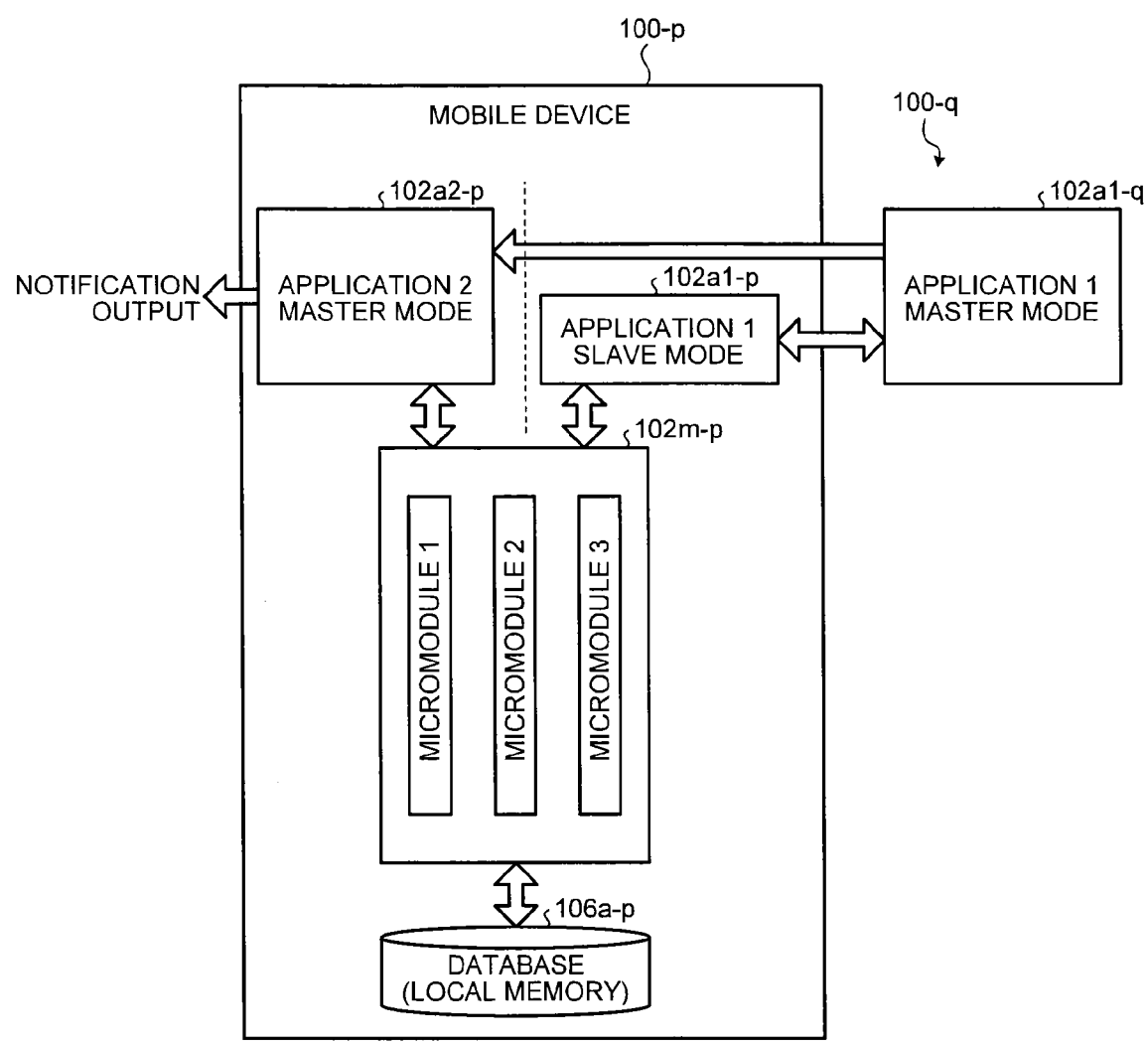
FIG. 12 is a diagram of Example where matching to an alert condition and a part of a data analysis are performed on a device.
Figure 13:
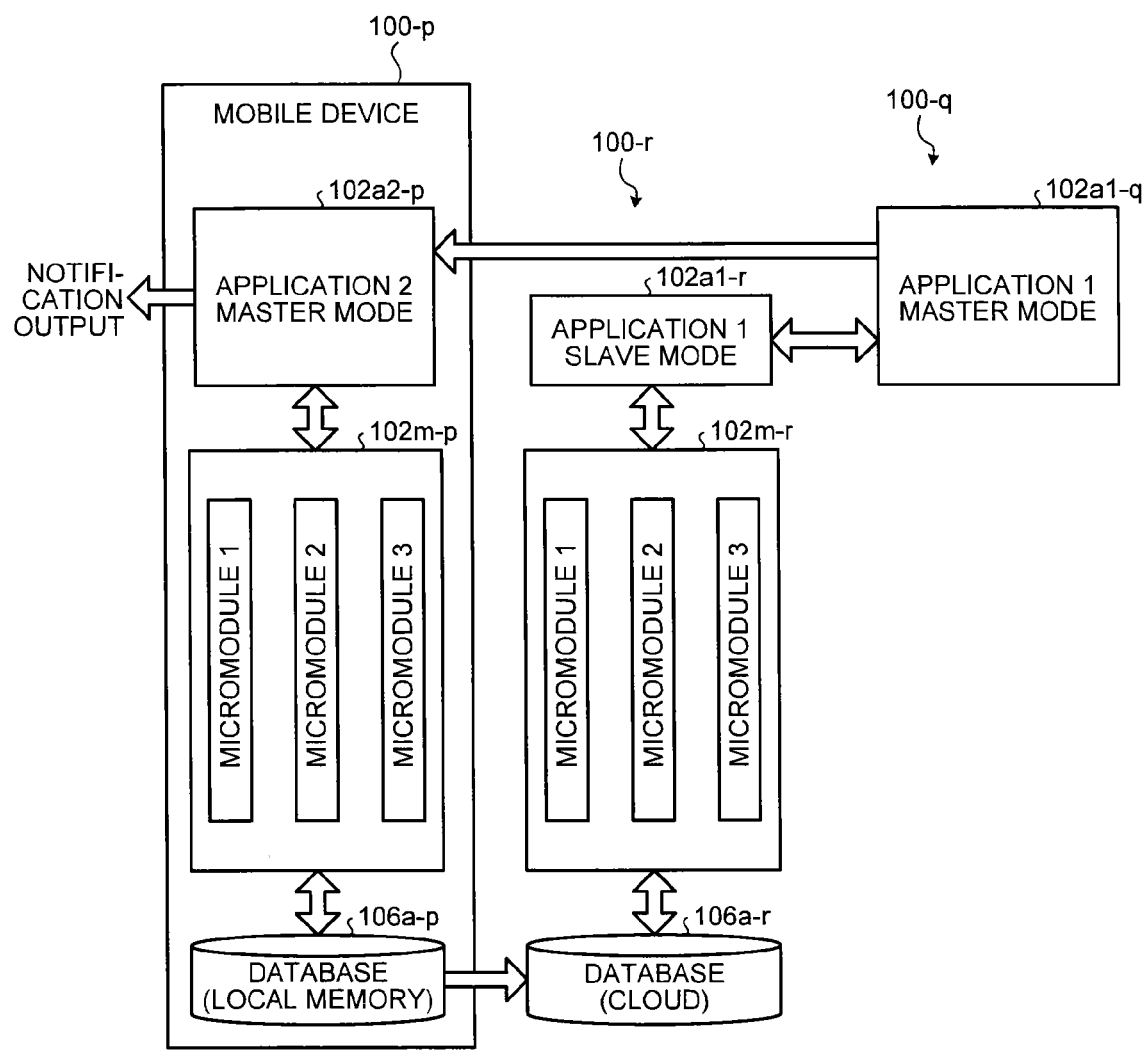
FIG. 13 is a diagram of Example where data is anonymized, automatically transferred to a server, and analyzed on the server and only matching to the alert condition is performed on the device.

The system according to this Second Example can realize the identification of the patient group who need the strict dose management, notification to the respective patients, and an appropriate feedback related to the deviation of the taking pattern. Here, FIG. 12 is a diagram of Example where matching to an alert condition and a part of a data analysis are performed on a device. FIG. 13 is a diagram of Example where data is anonymized, automatically transferred to a server, and analyzed on the server and only matching to the alert condition is performed on the device.

In the case of this Second Example, the basic configuration accumulates data including the user ID, the name of medicine, the dosing date and time, and the dosage, as medicine-taking data. Simultaneously, in the case of the configuration where the user takes a photograph of the medicine to be dosed for recording for each dose, the user ID and the combination of the photograph where the medicine is taken and the photographing time and date are accumulated as primary information. When this photograph is used, the name of medicine and the volume are determined by automatic image recognition or by human to convert the determination result into the combination of the user ID, the name of medicine, the dosing date and time, and the dosage. When a special device embedded in the medicine or a dose monitoring device using a chemical substance is used, the data from this device is also accumulated in the database 106*a*.

Simultaneously, if the information related to the dosing instruction from the doctor can be obtained by the input from the user him/herself or the medical institution, this information is also accumulated in the database 106*a* as data. This information is the combination of the user ID, the name of medicine, and the taking pattern. Furthermore, regularly or at the timing based on the user's free will, the data where the health status is described is recorded and accumulated in the database 106*a*. This data is, for example, the combination of: the time and date; and the information such as fine feeling and occurrence of a mild attack. As the user attribute, the name of the diagnosed disease or the like is recorded.

From these pieces of data, in the case of the patient having a certain disease, it is possible to determine that a problem such as seizure occurrence based on the analysis on the database 106*a* when the medicine is not taken continuously for 24 hours. In this case, the dose state is checked at a frequency of, for example, every hour. When the state where the medicine is not taken at a scheduled time is detected, the patient him/herself or the doctor is cautioned based on a certain rule, for example, "the caution in the first phase is issued when more than six hours passes since a scheduled taking time." Furthermore, when the medicine is not taken for 12 hours, for example, the caution in the second phase is issued.

Furthermore, when it is understood that this problem is unique to the user having a specific genetic background, the personal genome information can be used to narrow down the caution target. For example, when the patient who is diagnosed as a disease of X, has a specific variation in a gene of W, has a blood pressure of 145 or more, and is taking a medicine A does not take the medicine for 48 hours, for example, a caution is issued.

Third Example

Next, according to this embodiment, Third Example related to the system for realizing the share of information between departments of a pharmaceutical company or the like will be explained below.

Firstly, the background of the establishment of the system in this Third Example will be explained. Often in a pharmaceutical company or the like, the database related to unique information is established for each department and cannot be often easily accessed from another department. However, permitting the access while imposing a certain restriction allows meeting the needs required by the other department and might contribute to corporate activities.

Figure 14:
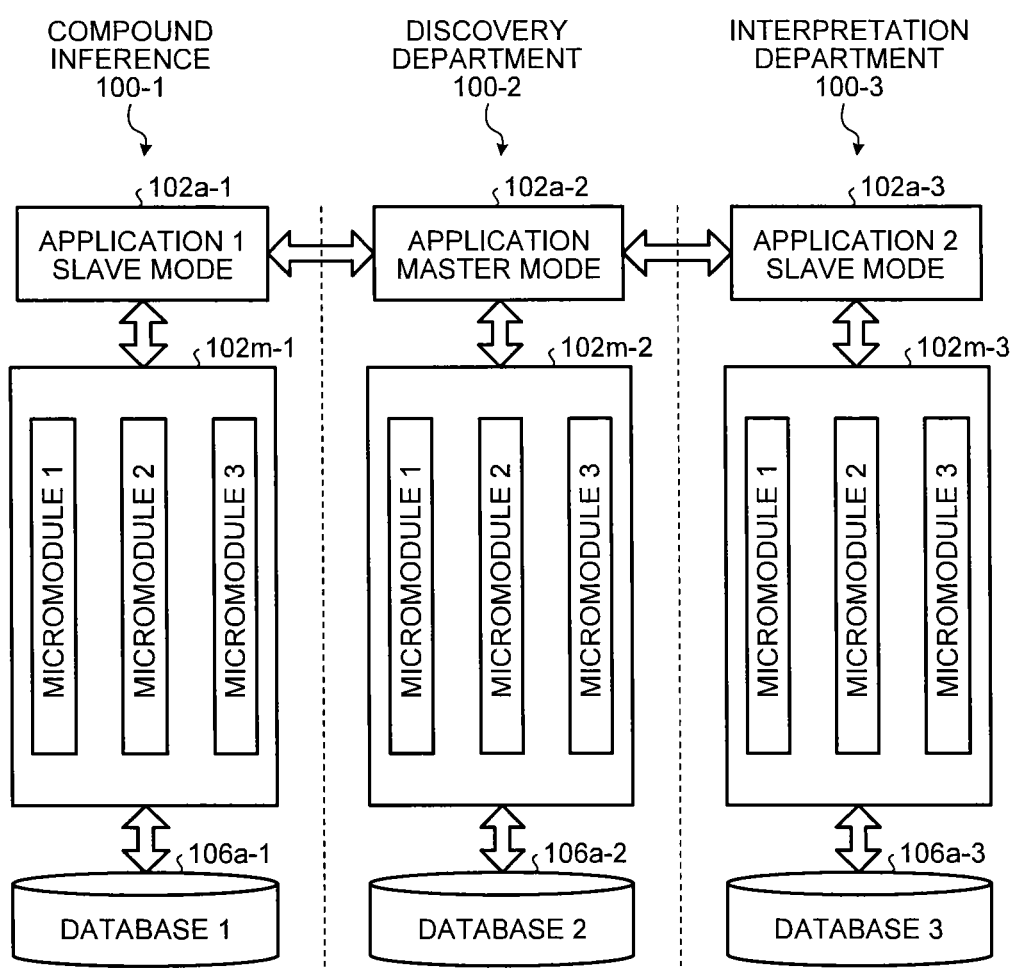

This relationship is also satisfied between: the company who creates a compound library or performs screening; and a pharmaceutical company to be a potential client of that company or outside researchers who analyzes the effectiveness of the compound. For example, the situation that the access of the discovery department in charge of development of a new medicine to the data of another candidate medicine already at a preclinical stage allows narrowing down the medicine discovery target of a related new medicine can be easily assumed. Furthermore, as the result of these examinations, assume that the progress of the development using a compound having a certain feature is determined to be preferred. However, the information of the compound exists in the database of another department or the acquired company or the like and might not be always freely accessed. At this time, the database is analyzed under a certain restriction possible in this embodiment to allow searching whether that compound is held or the like. FIG. 14 is a diagram of an information sharing system example between the departments of a pharmaceutical company or the like.

Figure 15:
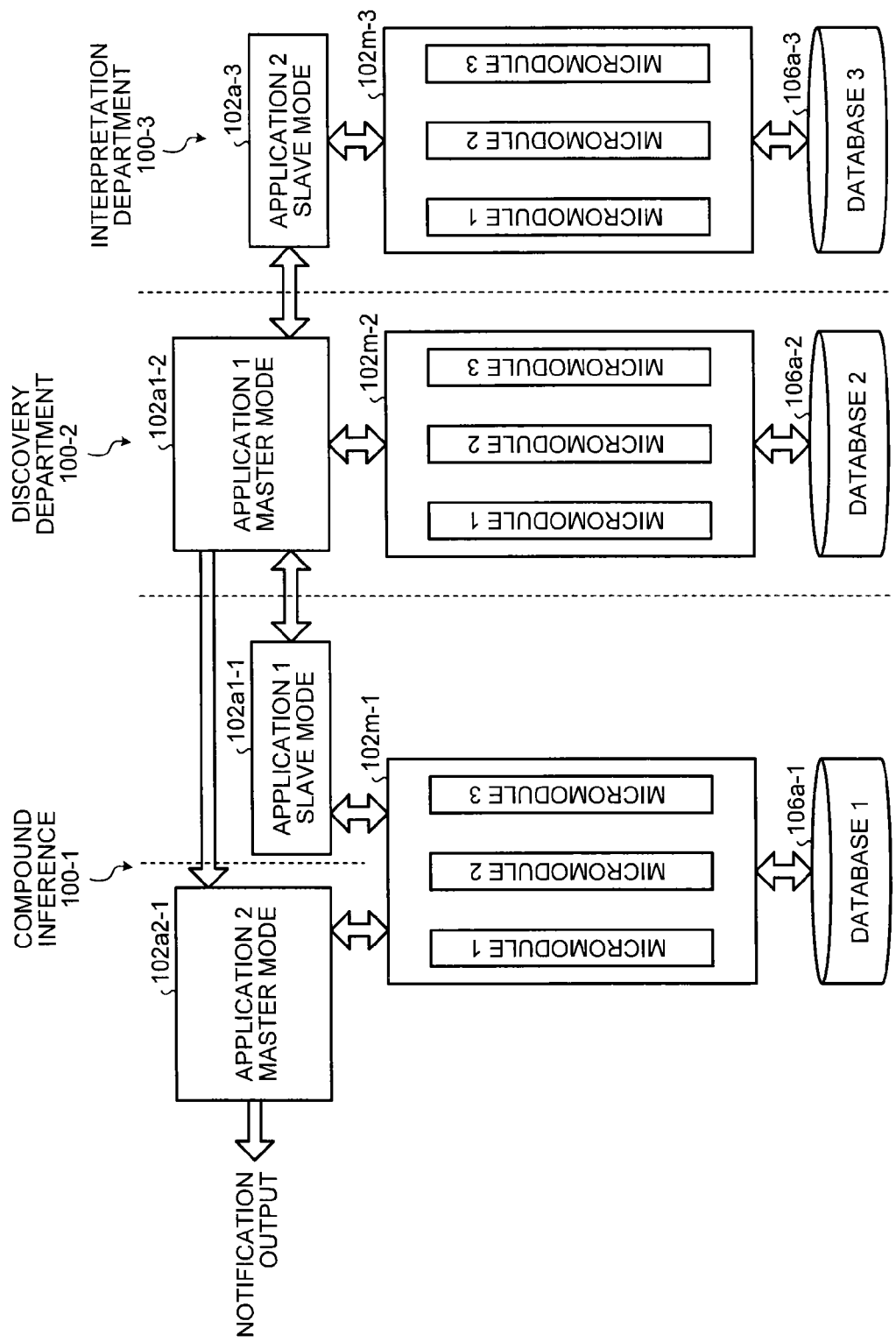
FIG. 15 is a schematic diagram of the process for performing a notification output process in Third Example.

As shown in FIG. 14, the application (102*a*-2) of the discovery department is a master application. This is because the application is a program for accessing the system of another department from the system of the discovery department. It is possible to set the program in the slave mode also to the database 106*a*-2 of the discovery department and access the database only via this program as setting. Here, FIG. 15 is a schematic diagram of the process for performing a notification output process in Third Example.

As a result of search, when it is determined that this compound is held, the program identical to the analysis program that has determined that the compound matches the desired condition is executed on the server having the database 106*a*-1. As shown in FIG. 15, this allows notifying the corresponding department and providing this compound to the discovery department. In this process, the secret information related to the structure of the possible substance is not directly taken to the outside of the corresponding department and allows this search and notification process.

Figure 16:
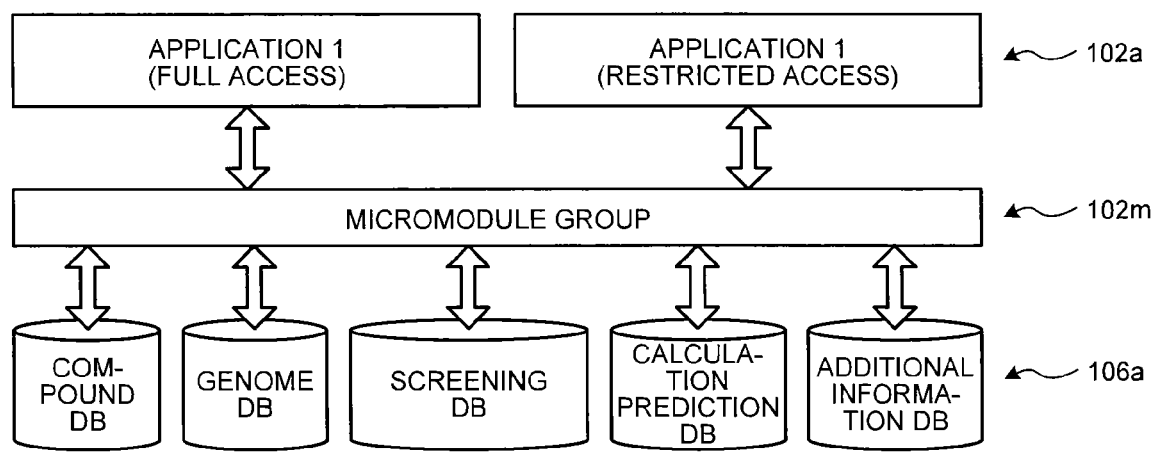
FIG. 16 is a diagram of the aggregation of a plurality of databases.

With this method, the company who has an effective compound library and intends to sell the compound library to a pharmaceutical company allows the pharmaceutical company to search the library without disclosing all the important information. This can lead to licensing of the compound matching the needs of the pharmaceutical company. With this method, the pharmaceutical company can perform searching while a sequence of searches is not known from the outside of the company, identify an interesting compound, and notify the partner company about the result alone. This allows keeping the security of the information such as development policy. Here, FIG. 16 is a diagram of the aggregation of a plurality of databases. As shown in FIG. 16, in Third Example, the respective databases may be the aggregation of a plurality of databases.

Fourth Example

Next, according to this embodiment, Fourth Example that comprehensively analyzes the medical data existing in a plurality of hospitals or the like to provide the information for improving the quality of the medical practice as necessary will be explained.

For example, when a plurality of medical institutions is presided over or a consultation is conducted for these medical institutions, it is necessary to analyze the medical information such as medical records accumulated in the respective medical institutions. However, the access to these pieces of information is restricted from the aspect of personal information protection or the like. Therefore, the mechanism claimed in this application is used to allow the department that performs integral analysis to perform restricted access and perform analysis based on this information. As a result, in the information contributing to an individual patient or improvement of the medical practice in an individual medical institution, a part whose effectiveness is increased by analysis without access restriction undergoes the execution of the application program without imposing access restriction to provide these pieces of information (see FIG. 15 as a diagram of an analysis system example for medical data between a plurality of hospitals while "compound inference" is replaced by "hospital 1," "discovery department" is replaced by "hospital group HQ," and "interpretation department" is replaced by "hospital 2").

For example, between a hospital group and partner medical institutions, certain analysis is made possible also when there are various restrictions related to data access. As a result, this contributes to improvement of the medical practice or the like of the medical group and the partner medical institutions.

For example, based on the medical record information and the prescription information accumulated in the respective databases 106a-1 to 3, regarding a specific disease, the average treatment success rate and the highest treatment success rate in this hospital group can be analyzed. Simultaneously, in this hospital group, regarding this illness, it is possible to identify the group or the attending physician who does not have a good treatment result. In this case, it is possible to instruct the attending physician identified here to introduce the method where the best treatment result is achieved.

Furthermore, for example, when it is found that a specific hospital uses a small amount of the generic drug having the identical effectiveness, these statistics can be notified to the attending physician. When notification is not made to the attending physician of an individual patient, these analyses can be performed within a single medical institution or by the analysis company having a contract with the institution without using the present invention. However, the effectiveness of analysis is considerably decreased. In the present invention, while the security is maintained, a plurality of medical institutions is exhaustively analyzed. Furthermore, it is possible to provide information to individual instances. This is excellent in improvement of the service quality and in cost management of the hospital group.

Authentication of Security Level

Figure 17:
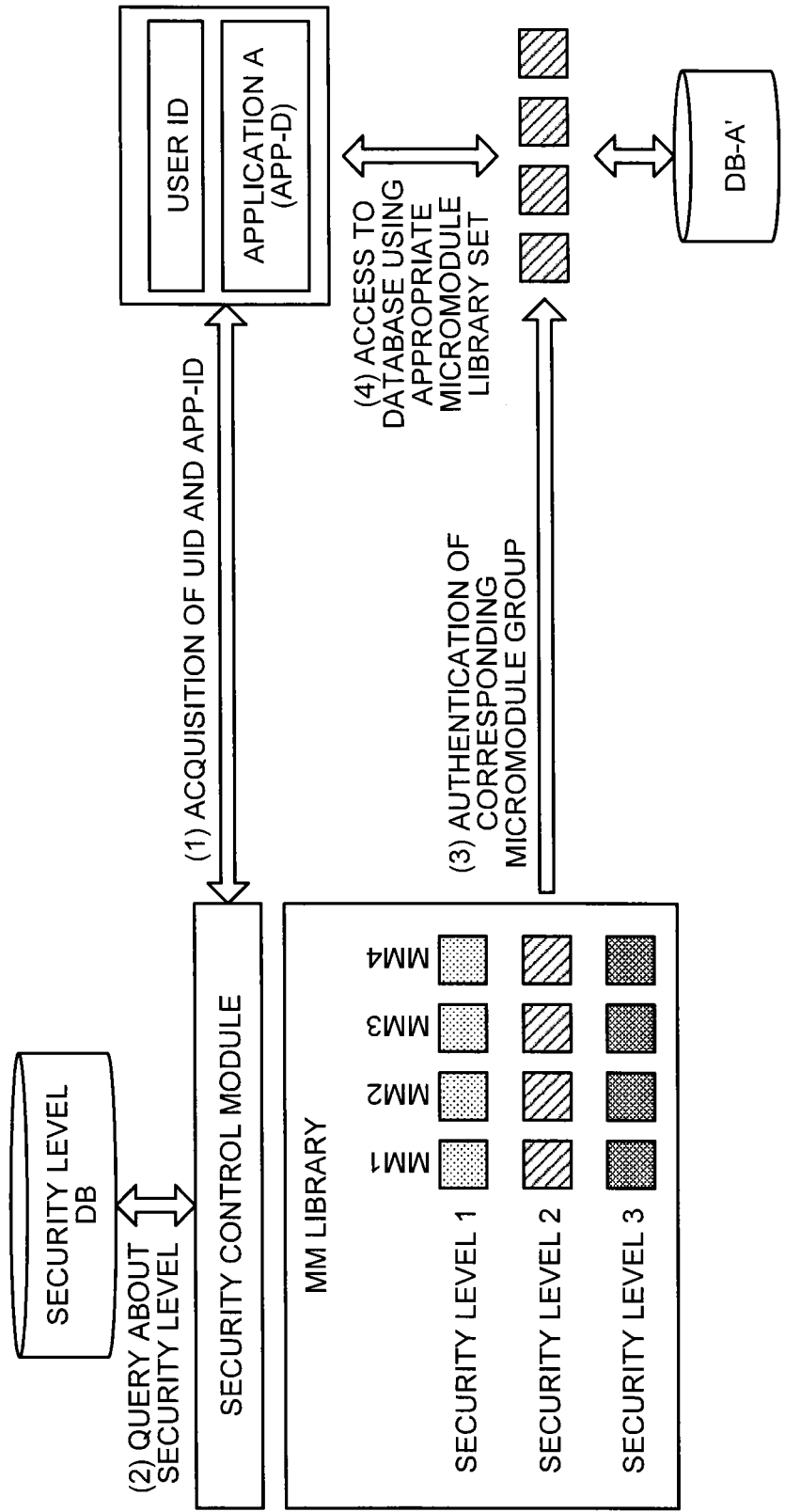
FIG. 17 is a schematic diagram of a security control example using a security controlling unit 102c.

Finally, according to this embodiment, the authentication example of the security level will be explained. Here, FIG. 17 is a schematic diagram of a security control example using the security controlling unit 102c.

Figure 18:
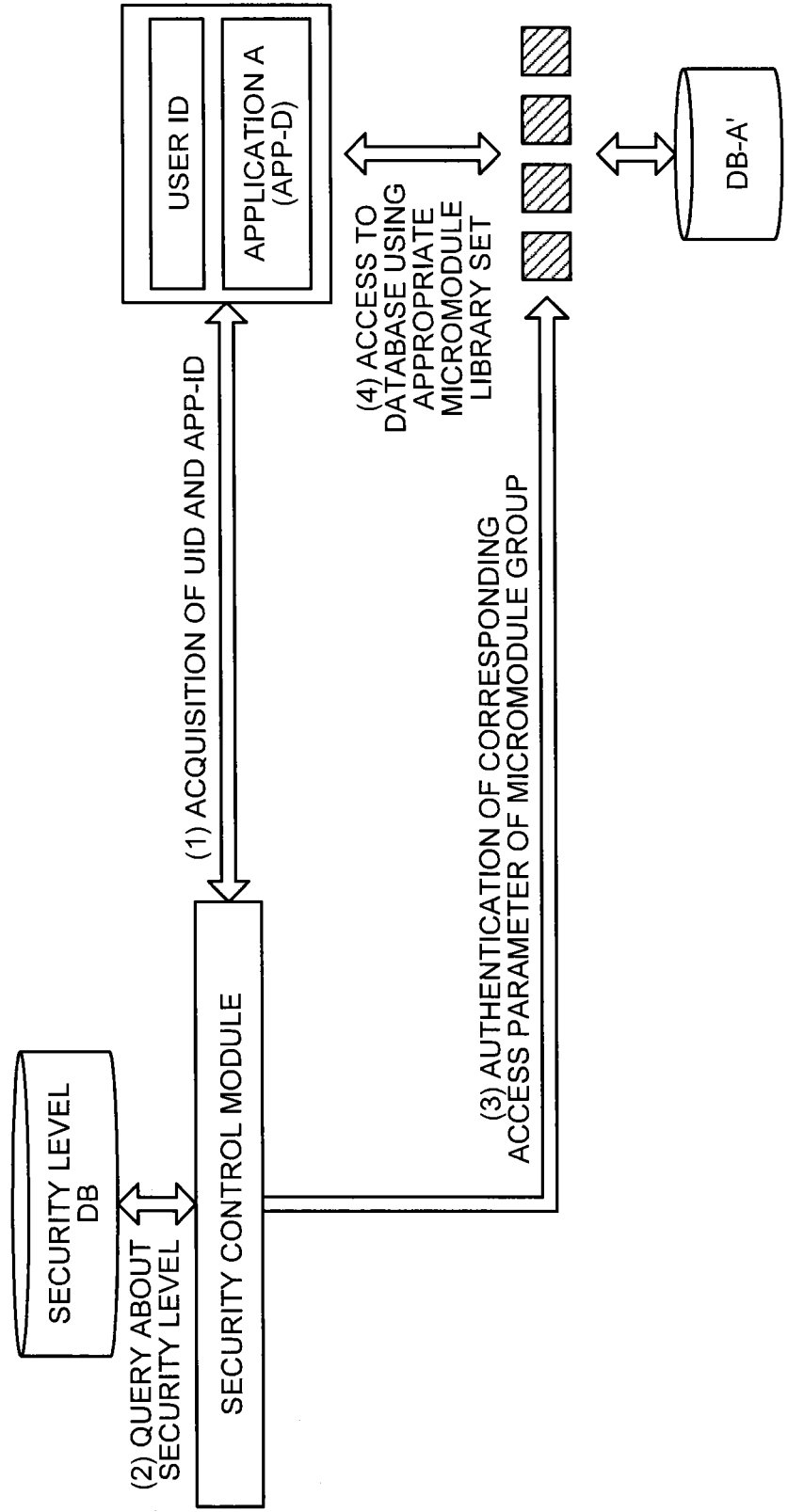
FIG. 18 is a schematic diagram of another example of the security control.

According to this embodiment, which level of the access to be permitted to the database 106a is determined mainly by the content of the application and the attribute of the user. For example, when an application A is executed by a user X, which level of the DB access to be allowed may be determined as follows. The security controlling unit 102c (security control module) that controls executions of all the applications on this DB queries the security database about the application ID (APP-ID) and the user ID (UID). As a result, based on the security level provided, which micromodule set usable by the application and the user is determined. When this application is executed by this user, it is possible to access the database 106a only through the micromodule set determined here. FIG. 18 is a schematic diagram of another example of the security control.

As shown in FIG. 18, as another implementation, each micromodule 102m may have the function for controlling the access to the database 106a corresponding to the security level. It is possible to perform the access corresponding to the security level obtained corresponding to the application and the user attribute when the access is requested from the application.

In addition, it is possible to incorporate an ordinarily performed method for authorizing the security level including a known method in this process.

Other Embodiments

The embodiments according to the present invention have been explained above. However, the present invention may be executed in not only the embodiment described above but also various different embodiments within the technical idea described in the scope of claims.

For example, the case where the data analysis apparatus 100 performs the process in a stand-alone configuration has been explained as one example. However, the data analysis apparatus 100 may perform the process corresponding to the request from the client terminal (in the chassis separately from that of the data analysis apparatus 100) to return the process result to the client terminal.

In the respective processes explained in the embodiments, all or a part of the process explained as the automatic process may be manually performed. Alternatively, all or a part of the process explained as the manual process may be automatically performed by a known method.

In addition, it is possible to optionally change the processing procedure, the control procedure, the specific names, the registration data in the respective processes, the information including the parameters such as the search condition, the screen examples, the database configurations described in the above-described literatures and drawings unless otherwise stated.

Regarding the data analysis apparatus 100, the respective components shown in the drawings are functional and conceptual and need not to be physically configured as shown in the drawings.

For example, regarding the processing functions that the respective devices of the data analysis apparatus 100 have, in particular, the respective processing functions performed in the control unit 102, all or any part of the processing functions may be realized by a Central Processing Unit (CPU) and the program that is interpreted and executed by this CPU or may be realized as hardware by wired logic. The program includes the programmed instruction for causing the computer to execute the method according to the present invention described later. The program is recorded in a recording medium that is non-transitory and computer-readable and is mechanically read by the data analysis apparatus 100 as necessary. That is, in the storage unit 106 or the like of a ROM, a Hard Disk Drive (HDD), or the like, the computer program for providing instructions to the CPU in collaboration with an Operating System (OS) and perform various processes is recorded. This computer program is loaded into a RAM to be executed and configures the control unit in collaboration with the CPU.

This computer program may be stored in the application program server coupled to the data analysis apparatus 100 via the optional network 300. All or a part of the computer program may be downloaded as necessary.

The program according to the present invention may be stored in a computer-readable recording medium or may be configured as a program product. Here, this "recording medium" includes any "portable physical medium" such as a memory card, a USB flash drive, a SD card, a flexible disk, a magnetic optical disk, a ROM, an EPROM, an EEPROM, a CD-ROM, an MO, a DVD, and a Blu-ray (registered trademark) Disc.

The "program" is a data processing method described in any language or description method, and may be in any format such as a source code and a binary code. Here, the "program" is not limited to be singularly configured, and includes a dispersed configuration as a plurality of modules or libraries and a configuration that achieves the function in collaboration with another program typified by an Operating System (OS). The specific configuration, the reading procedure, the installing procedure after reading, or the like for reading the recording medium in the respective devices shown in the embodiments may employ well-known configurations and procedures.

The various databases and the like (the databases 106a and the like) stored in the storage unit 106 are storage unit such as a memory device such as a RAM and a ROM, an immovable disk unit such as a hard disk, a flexible disk, and an optical disk, and store various programs, tables, databases, files for web pages, and the like for providing various processes and websites.

The data analysis apparatus 100 may be constituted as a known desktop or laptop personal computer, a mobile terminal device such as a mobile phone, a smart phone, a PHS, and a PDA and an information processing device such as a workstation. This information processing device may be constituted to be coupled to any peripheral device. The data analysis apparatus 100 may be realized by implementing the software (including a program, data, and the like) for realizing the method according to the present invention in this information processing device.

Further, the specific configuration of the dispersion or the integration of the devices is not limited to the illustrated configuration. All or a part of the illustrated configuration may be functionally or physically dispersed or integrated by any unit corresponding to various additions or the like or corresponding to the functional load. That is, the above-described embodiments may be carried out in any combination or the embodiment may be selectively carried out.

INDUSTRIAL APPLICABILITY

As described above in detail, the present invention allows providing the data communication system, the data analysis apparatus, the data communication method, and the program product that allow analysis by disclosing disclosable data while protecting data as a secret target and that allow performing data communication of the information obtained as an analysis result between persons, organizations, or the like having different access levels. In particular, the present invention is extremely effective in various fields of medical treatment, medicine production, medicine discovery, study of biology, and the like.

EXPLANATIONS OF LETTERS OR NUMERALS

100 DATA ANALYSIS APPARATUS
102 CONTROL UNIT
102a PROGRAM EXECUTING UNIT
102aLM ANALYSIS/INFERENCE ENGINE
102aL LEARNING MODULE
102aM META-REASONING MODULE
102b COMMUNICATION CONTROLLING UNIT
102c SECURITY CONTROLLING UNIT
102m MICROMODULE
106 STORAGE UNIT
106a DATABASE
106a1 PERSONAL HEALTH DATABASE
106a2 DRUG DATABASE
106a3 DISEASE DATABASE
106a4 BIOLOGICAL NETWORK DATABASE
106a5 MOLECULE DATABASE
106a7 PERSONAL GENOME DATABASE
106a8 HIGH-THROUGHPUT DATABASE
106a9 EXTERNAL HUMAN GENOME DATABASE
200 TERMINAL (MONITOR DEVICE OR THE LIKE)
214 OUTPUT UNIT
216 INPUT UNIT
300 NETWORK
600 EXTERNAL DEVICE

The invention claimed is:

1. A data communication system comprised of data analysis apparatuses communicatively coupled to one another, each of the data analysis apparatuses including storage circuitry and control circuitry, wherein
the storage circuitry includes a database that stores data,
the control circuitry includes:
a data accessing unit implemented by the control circuitry that accesses the database at a given access level,
a program executing unit implemented by the control circuitry that executes an application program based on the data acquired at the given access level from the database via the data accessing unit to perform data analysis, and
a communication controlling unit implemented by the control circuitry that performs communication control to allow transmission and reception of a data analysis result by the program executing unit implemented by the control circuitry with respect to an other of the data analysis apparatuses where the access level is different from the given access level,
the other of the data analysis apparatuses has the given access level to allow specifying a target,
the program executing unit implemented by the control circuitry of the other of the data analysis apparatuses refers to the database based on the received data analysis result to specify the target and output notification regarding the specified target, and
the program executing unit implemented by the control circuitry performs the data analysis using a data analysis method from among Genome Wide Association Study (GWAS), Conditional Genome-Wide Association Study (conditional GWAS), Genome-Wide Network-based Association Study (GNAS), and Conditional GNAS.

2. The data communication system according to claim 1, wherein the data accessing unit implemented by the control circuitry includes a micromodule group that accesses the database at respective different access levels.

3. The data communication system according to claim 1, wherein, while the program executing unit implemented by the control circuitry executes the application program in a master mode, the program executing unit implemented by the control circuitry of another of the data analysis apparatuses executes the application program in a slave mode based on acquisition of the data depending on the access level at the master mode side via the data accessing unit implemented by the control circuitry.

4. The data communication system according to claim 1, wherein the database is a personal health database that stores medical information including one of medical record information, drug prescription data, medication intake data, health examination data, subjective symptom information, and behavior record data of an individual person, as the data.

5. The data communication system according to claim 1, wherein
the access level that allows specifying a target is given to a person related to a medical institution including a doctor, and
the access level that does not allow specifying a target is given to a user of a database open to an outside.

6. The data communication system according to claim 1, wherein the data analysis result received by the other of the data analysis apparatuses does not identify the target.

7. A data analysis apparatus comprising:
storage circuitry; and
control circuitry,
wherein
the data analysis apparatus is communicatively coupled to other data analysis apparatuses,
the storage circuitry includes a database that stores data,
the control circuitry includes:
a data accessing unit implemented by the control circuitry that accesses the database at a given access level,
a program executing unit implemented by the control circuitry that executes an application program based on the data acquired at the given access level from the database via the data accessing unit to perform data analysis, and
a communication controlling unit implemented by the control circuitry that performs communication control to allow transmission and reception of a data analysis result by the program executing unit implemented by the control circuitry with respect to an other of the data analysis apparatuses where the access level is different from the given access level,
the other of the data analysis apparatuses has the given access level to allow specifying a target, and
a program executing unit implemented by control circuitry of the other of the data analysis apparatuses refers to the database based on the received data analysis result to specify target and output notification regarding the specified target, and
the program executing unit implemented by the control circuitry performs the data analysis using a data analysis method from among Genome Wide Association Study (GWAS), Conditional Genome-Wide Association Study (conditional GWAS), Genome-Wide Network-based Association Study (GNAS), and Conditional GNAS.

8. A data communication method executed by a data communication system where data analysis apparatuses are communicatively coupled to one another, each of the data analysis apparatuses including storage circuitry and control circuitry, wherein
the storage circuitry includes a database that stores data, the method, executed by the data communication system, comprises:
accessing the database at a given access level, said accessing being executed by the control circuitry of one of the data analysis apparatuses of the data analysis apparatuses;
executing an application program based on the data acquired from the database at the given access level at said accessing to perform data analysis, said executing the application program being executed by the control circuitry of the one of the data analysis apparatuses;
transmitting a data analysis result at said executing the application program to an other of the data analysis apparatuses where the access level is different from the given access level, said transmitting being executed by the control circuitry in the one of the data analysis apparatuses; and
receiving the data analysis result from the other of the data analysis apparatuses, said receiving being executed by the control circuitry of the other of the data analysis apparatuses,
the other of the data analysis apparatuses has the given access level to allow specifying a target,
a program executing unit implemented by the control circuitry of the other of the data analysis apparatuses refers to the database based on the received data analysis result to specify the target and output notification regarding the specified target, and
the data analysis is performed using a data analysis method from among Genome Wide Association Study (GWAS), Conditional Genome-Wide Association Study (conditional GWAS), Genome-Wide Network-based Association Study (GNAS), and Conditional GNAS.

9. A computer program product having a non-transitory tangible computer readable medium including programmed instructions for causing, when executed by a data analysis apparatus including storage circuitry that includes a database storing data, and control circuitry, the data analysis apparatus being communicatively coupled to other data analysis apparatuses, the control circuitry to perform a data communication method comprising:
accessing the database at a given access level;
executing an application program based on the data acquired at the given access level from said accessing to perform data analysis; and
performing communication control to allow transmission and reception of a data analysis result at said executing with respect to an other of the data analysis apparatuses where the access level is different from the given access level, wherein
the other of the data analysis apparatuses has the given access level to allow specifying a target,
a program executing unit implemented by control circuitry of the other of the data analysis apparatuses refers to the database based on the received data analysis result to specify the target and output notification regarding the specified target, and
the data analysis is performed using a data analysis method from among Genome Wide Association Study (GWAS), Conditional Genome-Wide Association Study (conditional GWAS), Genome-Wide Network-based Association Study (GNAS), and Conditional GNAS.

* * * * *